United States Patent [19]
Gubin et al.

[11] Patent Number: 5,223,510
[45] Date of Patent: Jun. 29, 1993

[54] ALKYLAMINOALKYL DERIVATIVES OF BENZOFURAN, BENZOTHIOPHENE, INDOLE AND INDOLIZINE, PROCESS FOR THEIR PREPARATION AND COMPOSITIONS CONTAINING THEM

[75] Inventors: Jean Gubin; Pierre Chatelain, both of Brussels; Jean Lucchetti, Chastre; Gilbert Rosseels; Henri Inion, both of Wemmel, all of Belgium

[73] Assignee: Sanofi, Paris, France

[21] Appl. No.: 736,580

[22] Filed: Jul. 26, 1991

[30] Foreign Application Priority Data

Aug. 6, 1990 [FR] France ................. 90 10036

[51] Int. Cl.$^5$ ............... C07D 237/28; C07D 31/34; C07D 333/72; C07D 409/06; A61K 31/44; A61K 31/435; A61K 31/50; A61K 31/40

[52] U.S. Cl. ......................... 514/299; 549/399; 549/404; 549/405; 549/407; 549/408; 549/410; 549/419; 549/420; 549/52; 549/55; 549/59; 549/60; 549/74; 549/75; 549/76; 549/398; 514/403; 514/443; 514/469; 514/470; 544/212; 546/112; 546/121; 546/183; 548/214; 548/452; 548/466; 548/469; 548/490; 548/491; 548/492; 548/493

[58] Field of Search ............ 546/121, 112, 183; 544/212; 514/299, 233.2, 253, 913, 228, 232, 403, 443, 469, 470; 548/214, 452, 466, 469, 490, 491, 492, 493; 549/52, 55, 59, 60, 74, 76, 398, 399, 404, 405, 407, 408, 410, 419, 420

[56] References Cited

U.S. PATENT DOCUMENTS

| | | | |
|---|---|---|---|
| 3,947,470 | 3/1976 | Brenner et al. | 549/57 |
| 4,024,273 | 5/1977 | Brenner et al. | 549/57 |
| 4,103,012 | 7/1978 | Gubin et al. | 514/299 |
| 4,117,128 | 9/1978 | Brenner | 514/212 |
| 4,520,026 | 5/1985 | Rosseels et al. | 514/299 |
| 4,559,346 | 12/1985 | King | 514/297 |
| 4,567,270 | 1/1986 | Chorvat et al. | 546/183 |
| 4,957,925 | 9/1990 | Gubin et al. | 546/121 |
| 4,994,474 | 2/1991 | Gubin et al. | 546/121 X |
| 5,017,579 | 5/1991 | Gubin et al. | 514/299 |

FOREIGN PATENT DOCUMENTS

| | | | |
|---|---|---|---|
| 338746 | 4/1989 | European Pat. Off. | 514/299 |
| 360784 | 9/1989 | European Pat. Off. | 514/299 |
| 8902888 | 4/1989 | World Int. Prop. O. | 514/299 |
| 8902892 | 4/1989 | World Int. Prop. O. | 514/299 |
| 8902893 | 4/1989 | World Int. Prop. O. | 514/299 |

*Primary Examiner*—Floyd D. Higel
*Attorney, Agent, or Firm*—Wegner, Cantor, Mueller & Player

[57] ABSTRACT

The subject of the invention is benzofuran, benzothiophene, indole or indolizine compounds of general formula:

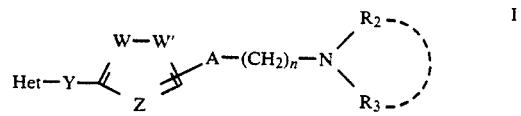

in which: Het represents one of the groups:

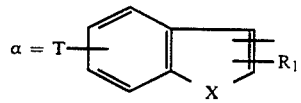

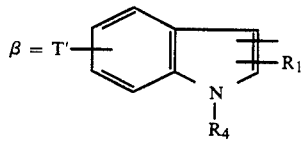

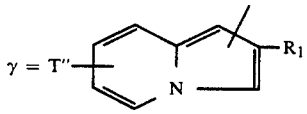

in which
T,T' and T"represent particularly a group:

R and $R_a$, identical or different, represent
X represent —O— or —S—
Y represents a radical
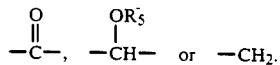
These compounds are useful as medecines particularly for the treatment of pathological syndroms of the cardio-vascular system.
26 Claims, No Drawings

ALKYLAMINOALKYL DERIVATIVES OF BENZOFURAN, BENZOTHIOPHENE, INDOLE AND INDOLIZINE, PROCESS FOR THEIR PREPARATION AND COMPOSITIONS CONTAINING THEM

The present invention relates, in a general manner, to new heterocyclic derivatives as well as to a process for their preparation.

In particular, the invention relates to derivatives of benzofuran, benzothiophene, indole and indolizine, which may be represented by the general formula:

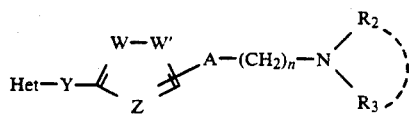    I in which: Het represents one of the groups:

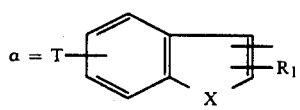

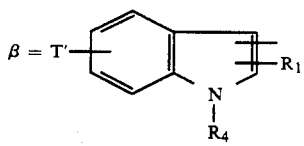

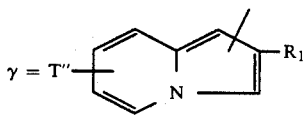

in which: T represents a group:

in which:
R and Ra, identical or different, represent:
hydrogen,
a $C_1$–$C_4$ alkyl radical,
a —$SO_2R'$ radical in which R' represents a linear or branched $C_1$–$C_6$ alkyl radical, a trifluoromethyl radical, a phenyl radical optionally substituted by a $C_1$–$C_4$ alkyl radical, a benzyl radical optionally substituted by a $C_1$–$C_4$ alkyl radical or a benzoyl radical optionally substituted by a $C_1$–$C_4$ alkyl radical, Ra and R' being capable of forming with the nitrogen atom of a sulfonamido group a ring containing from 3 to 6 carbon atoms, T' represents:
hydrogen,
a nitro group,
a

group as previously defined,

T" represents:
a benzyloxycarbamoyl group,
a group:

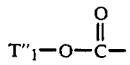

in which $T''_1$ represents hydrogen or a $C_1$–$C_4$ alkyl group
a group:

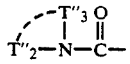

in which $T''_2$ and $T''_3$, identical or different, represent hydrogen or a $C_1$–$C_4$ alkyl group or $T''_2$ and $T''_3$ form with the nitrogen atom to which they are attached a ring having from 4 to 6 carbon atoms,
a

group as previously defined,
X represents —O— or —S—
Y represents a

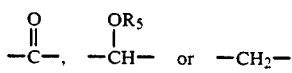

radical in which $R_5$ represents hydrogen, a $C_1$–$C_4$ alkyl radical or an acyl radical of formula

in which $R'_4$ represents a $C_1$–$C_4$ alkyl radical
$R_1$ represents a $C_1$–$C_6$ alkyl radical, a phenyl radical optionally substituted by a $C_1$–$C_4$ alkyl radical or a halogenophenyl radical
$R_2$ represents:
hydrogen,
a linear or branched $C_1$–$C_6$ alkyl radical
$R_3$ represents:
a linear or branched $C_1$–$C_6$ alkyl radical
a radical of formula:

in which Alk represents a simple bond or a linear or branched $C_1$–$C_5$ alkylene radical and $R_6$ represents a pyridyl, phenyl, phenoxy, 3,4-methylenedioxy phenyl radical or a phenyl group or phenoxy group substituted by one or more substituents, identical or different, selected from halogens, $C_1$–$C_4$ alkyl or $C_1$–$C_4$ alkoxy groups,
$R_2$ and $R_3$, when they are taken together, represent a $C_3$–$C_6$ alkylene or alkenylene radical, optionally substituted by a phenyl radical or optionally interrupted by —O—, —NH—, —N= or <N—$R_7$, $R_7$ representing a $C_1$–$C_4$ alkyl radical or phenyl radical
$R_4$ represents:
hydrogen,
a $C_1$–$C_4$ alkyl radical, a —$SO_2R'_1$ radical in which $R'_1$ represents a $C_1$-$C_4$ alkyl radical, a phenyl radical optionally substituted by a $C_1$-$C_4$ alkyl radical or a benzyl radical optionally substituted by a $C_1$-$C_4$ alkyl radical a

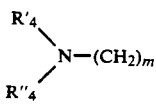

radical in which $R'_4$ and $R''_4$, identical or different, represent a $C_1$-$C_4$ alkyl radical and m represents an integer from 1 to 3

A represents —O—, —S— or

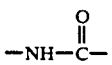

W, W' and Z are such that:
when W and W' are identical and represent

or N, Z represents —O— or —S—
when W represents

and W' represents

Z represents

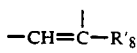

$R_8$ and $R'_8$ being identical or different and representing hydrogen, a halogen atom, for example fluorine, chlorine or bromine, a $C_1$-$C_4$ alkyl radical such as methyl or a $C_1$-$C_4$ alkoxy radical such as methoxy n represents an integer from 1 to 5, provided that when $R_4$ represents a —$SO_2R'_1$ radical, T' represents hydrogen, a nitro group or a cyclised

group.

In formula I above:

Het may represent, in particular, a 4-T benzofuran-2 or 3-yl, 5-T benzofuran-2 or 3-yl, 7-T benzofuran-2 or 3-yl, 4-T benzothien-2 or 3-yl, 5-T benzothien-2 or 3-yl, 7-T benzothien-2 or 3-yl, 4-T' indol-2 or 3-yl, 5-T' indol-2 or 3-yl, 7-T' indol-2 or 3-yl, 7-T" indolizin-1 or 3-yl radical R and $R_a$ may represent, in particular, a methyl, ethyl, n-propyl, isopropyl, n-butyl, isobutyl or tert.butyl radical $R_1$ may represent a methyl, ethyl, n-propyl, iso-propyl, n-butyl, isobutyl, tert.butyl, 1-methyl propyl, n-pentyl, neopentyl, n-hexyl, phenyl, mono-methylphenyl, mono-fluoro-mono-chloro or mono-bromo-phenyl radical, $R_2$ may represent, in particular, a methyl, ethyl, n-propyl, isopropyl, n-butyl, isobutyl, tert.butyl, n-pentyl, neopentyl or n-hexyl radical $R_3$ may represent, in particular, a methyl, ethyl, n-propyl, isopropyl, n-butyl, isobutyl, tert.butyl, 1-methyl propyl, n-pentyl, n-hexyl, phenyl, benzyl, phenethyl, methoxyphenyl, dimethoxyphenethyl radical, for example 3,4-dimethoxy phenethyl or 3,5-dimethoxy phenethyl, trimethoxyphenethyl, dimethylphenethyl, dimethoxybenzyl, pyridylethyl or a phenethyl radical substituted in the aromatic part by methyl and methoxy radicals, $R_2$ and $R_3$, taken together, may represent in particular a 1,4-tetramethylene; 1,5-pentamethylene; 3-oxo 1,5-pentamethylene; 3-aza 1,5-pentamethylene; 3-methylaza 1,5-pentamethylene; 3-phenylaza 1,5-pentamethylene or a —CH—CH—N=CH radical such that $R_2$ and $R_3$, taken together with nitrogen atom to which they are attached, may represent in particular a pyrrolidinyl, piperidinyl, morpholinyl, piperazinyl, 4-methyl piperazinyl, 4-phenyl piperazinyl or 1H-imidazolyl radical.

W, W' and Z, taken together with the carbon atoms to which they are attached, may form in particular a phenyl, furyl or thienyl radical.

One class of preferred compounds of the invention may be represented by the compounds of formula I in which R represents a —$SO_2R'$ groups and $R_a$ represents hydrogen. Similarly, one particular class of compounds of formula I is that in which Y represents a

radical.

Another class of preferred compounds is that in which the

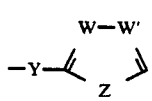

moiety represents a benzoyl radical.

Similarly, a particular class of compounds of formula I is that in which

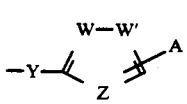

represents a 4-benzoyloxy radical.

Furthermore, the compounds of formula I in which X represents —O— are preferred compounds as are those in which the

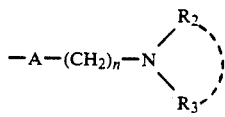

chain is found in position 4.

Finally, the compounds of formula I in which $R_1$, $R_2$ and $R_3$ represents a n-butyl radical and n denotes 3 may also be considered as being preferred.

The invention also relates to the pharmaceutically acceptable salts of the compounds of formula I formed from an organic or inorganic acid.

As examples of organic salts of this type, the oxalate, maleate, fumarate, methanesulfonate, benzoate, ascorbate, pamoate, succinate, hexamate, bismethylenesalicylate, ethanedisulfonate, acetate, propionate, tartratesalicylate, citrate, gluconate, lactate, malate, cinnamate, mandelate, citraconate, aspartate, palmitate, stearate, itaconate, glycolate, p-aminobenzoate, glutamate, benzenesulfonate, p-toluenesulfonate and theophylline acetate may be mentioned as well as the salts formed from an amino acid such as the salt of lysine or histidine.

As inorganic salts of this type, the hydrochloride, hydrobromide, sulfate, sulfamate, phosphate and nitrate may be mentioned.

It has been found that the compounds of the invention possess remarkable pharmacological properties since they have been found to be capable of prolonging in a uniform manner the action potential and the refractory period of the cells of the myocardium. Furthermore, most of the compounds of the invention have also shown bradycardiac, anti-hypertensive and antiadrenergic properties.

These properties are capable of making the compounds in question very useful in the treatment of certain pathological syndromes of the cardiovascular system, in particular in the treatment of angina pectoris, hypertension, arrhythmias and cerebral circulatory insufficiency.

In the antitumoral field, the compounds of the invention will be able to be used as potentiators of anticancer drugs.

Consequently, the invention also relates to pharmaceutical or veterinary compositions containing as active ingredient at least one compound of the invention, in combination with a suitable excipient or pharmaceutical vehicle.

Depending on the route of administration selected, the daily dose for a human being weighing 60 kg will vary between 2 and 500 mg of active ingredient.

The compounds of formula I can be prepared according to the following methods:

I—The compounds of formula I in which Y represents a

group may be obtained:

A—In the case in which T or T' represents an amino group, by hydrogenating a nitro derivative of general formula: II

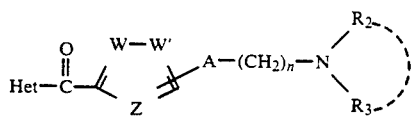

in which Het represents a group:

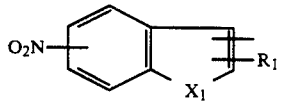

in which $X_1$ represents —O—, —S— or a $<$N—$R_4$ radical and $R_1$, $R_2$, $R_3$, A, W, W', X, Y, Z and n are as previously defined, the reaction taking place in the presence of a suitable catalyst such as platinum or palladium oxide, zinc in a hydrochloric acid medium or tin in a hydrochloric acid medium and in a polar solvent such as an alcohol for example ethanol, which leads to the formation of the desired compounds of formula I in the form of the free base.

B—In the case in which T, T' or T" represents a

group in which:

a) R represents a —$SO_2R'$ group and $R_a$ represents hydrogen or a —$SO_2R'$ group by reacting a compound of formula I in which R and $R_a$ each represents hydrogen with one or two equivalents of a halide of general formula:

$$Hal-SO_2-R' \quad\quad III$$

or an anhydride of general formula:

$$(R'SO_2)_2O \quad\quad IIIa$$

in which R' is as previously defined and Hal represents a halogen atom, for example chlorine or bromine, the reaction taking place in the presence of an acid acceptor and in a suitable organic solvent, which leads to the formation of the desired compounds of formula I in the form of the free base.

As acid acceptor, a compound of basic character is usually used such as an amine, for example triethylamine while the solvent may be an aprotic solvent such as dichloroethane or carbon tetrachloride.

b) R has the value indicated and $R_a$ represents an alkyl radical by reacting a derivative of formula I in which R has the value indicated and $R_a$ represents hydrogen in an alkaline medium with one or two equivalents of a halide of general formula:

$$R'_a-Hal \quad\quad IV$$

in which Hal is as previously defined and $R'_a$ represents a $C_1$-$C_4$ alkyl radical, which leads to the formation of the desired compounds of formula I in the form of the free base.

C—In the case in which T' represents a nitro group or T, T' or T" represents a cyclised

group, by reacting, in a suitable solvent usually a polar solvent such as N,N-dimethylformamide, acetonitrile or methyl ethyl ketone or an apolar solvent such as benzene or toluene, a compound of general formula:

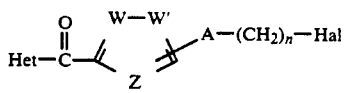

V in which A, W, W', Z, Hal and n are as defined previously and Het represents a group of general formula:

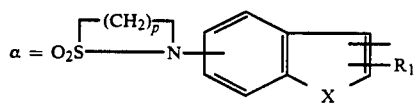

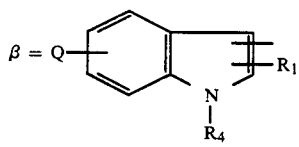

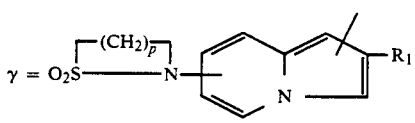

in which $R_1$, $R_4$ and X are as defined previously, Q represents a nitro group or

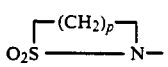

and p represents an integer from 1 to 4, with a nitrogenous compound of general formula:

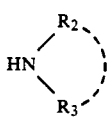

VI and in which $R_2$ and $R_3$ are as defined previously, the reaction taking place in the presence of a basic agent such as an alkali metal hydroxide or carbonate or an excess of the amine of formula VI which leads to the formation of the desired compounds of formula I in the form of the free base.

D—In the case in which T" represents a carbalkoxy group, by treating at a temperature from 80° to 110° C., an indolizine derivative of general formula:

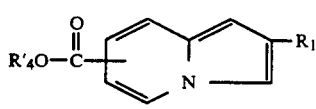

VII in which $R_1$ and $R'_4$ are as defined previously with a halide of general formula:

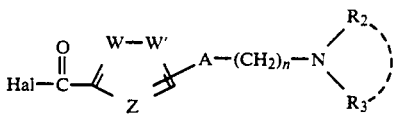

VIII in which Hal, A, $R_2$, $R_3$, W, W', Z and n are as defined previously, which leads to the formation of the desired compounds of formula I in the form of the free base.

E—In the case in which T" represents a carboxy group, by saponifying a carbalkoxy-indolizine derivative of formula I in which Het represents a group of general formula:

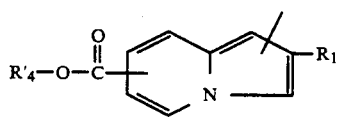

IX in which $R_1$ and $R'_4$ are as defined previously, by means of an alkali metal hydroxide, the saponification preferably taking place at the reflux temperature of the medium and in a suitable solvent such as an alcohol for example ethanol, to produce the desired compounds of formula I in the form of the free base.

F—In the case in which T" represents a benzyloxycarbamoyl group, by reacting a carboxy-indolizine derivative of formula I in which Het represents a group of general formula:

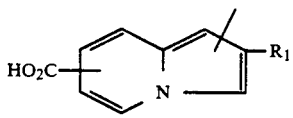

X in which $R_1$ is as defined previously, in a suitable solvent such as acetone and at a temperature from 0° to +10° C., with ethyl chloroformate in the presence of an acid acceptor such as an amine, for example triethylamine, then with an alkali metal azide and finally with benzyl alcohol, for example at a temperature from 90° to 110° C., to produce the desired compounds of formula I in the form of the free base.

G—In the case in which T" represents an amino group, by hydrogenating a benzyloxycarbamoyl-indolizine derivative of formula I in which Het represents a group of formula:

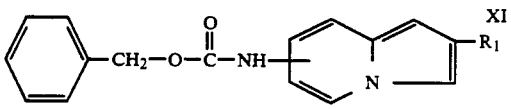

XI in which $R_1$ is as defined previously, in a suitable solvent such as an alcohol for example ethanol and in the presence of a suitable catalyst such as platinum or palladium to produce the desired compounds of formula I in the form of the free base.

H—In the case in which T" represents a substituted or unsubstituted carboxamido group, by heating at a temperature from 90° to 110° C. and in a suitable solvent such as alcohol a compound of formula I in which Het represents a group of formula X with a compound of general formula:

 XII in which T''$_2$ and T''$_3$ are as defined previously, which leads to the formation of the desired compounds of formula I in the form of the free base.

II—The compounds of formula I in which Y represents a

group may be obtained:

a) When R$_5$ represents hydrogen, by reducing a compound of formula I in which Y represents a

group by means of an alkali metal borohydride such as sodium borohydride and in a suitable solvent such as an alcohol or an ether, which leads to the formation of the desired compounds of formula I in the form of the free base.

b) When R$_5$ represents a R'$_4$ radical or an acyl radical of formula

by reacting the secondary alcohol thus formed, i.e. a compound of formula I in which Y represents a

group either with an alkali metal alcoholate, then with a halide of general formula:

 XIII in which Hal and R'$_4$ are as defined previously or with an acyl halide of general formula:

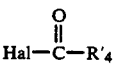 XIV in which Hal and R'$_4$ are as defined previously, the reaction taking place in the presence of an acid acceptor such as pyridine so as to produce the desired compounds of formula I in the form of the free base.

Depending on the structure of the starting material, mixtures of compounds may be obtained on reduction. The components of these mixtures may be separated according to standard techniques such as elution chromatography.

III—The compounds of formula I in which Y represents a —CH$_2$— group may be prepared, preferably by reducing by means of an alkali metal borohydride such as sodium borohydride in the presence of trifluoroacetic acid and in a suitable solvent such as an alcohol, an ether or a halogenated hydrocarbon, a compound of formula I in which Y represents a

group, which leads to the formation of the desired compounds of formula I in the form of the free base.

Usually, the reduction of the compounds of formula I in which Y represents a

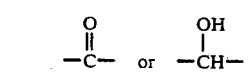

group is carried out at a temperature from $-10°$ to $+10°$ C., and preferably at $0°$ C.

Variants of the processes previously described may be used to prepare certain compounds of formula I, in particular compounds of formula I in which Y represents a

group.

Examples of such processes are described below:

I—When T' represents a nitro group or Y represents a

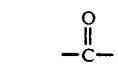

group a) An acyl halide of general formula:

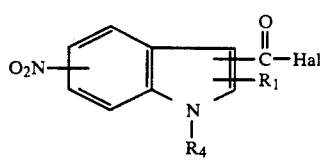 XV in which R$_1$, R$_4$ and Hal are as defined previously, is condensed in the presence of a Lewis acid such as aluminium chloride or stannic chloride with an amine of general formula:

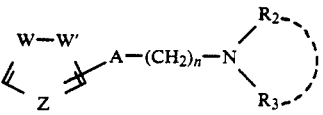 XVI in which A, R$_2$, R$_3$, W, W', Z and n are as defined previously, which leads to the formation of the desired compounds of formula I in the form of the free base.

II—When T' represents a nitro group or when T, T' or T'' represents a cyclised

group, Y represents a

group and A represents —O—, a ketone of general formula:

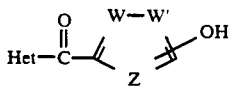

in which W, W' and Z are as defined previously and Het represents a group of general formula:

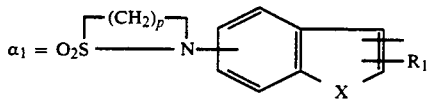

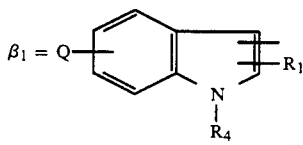

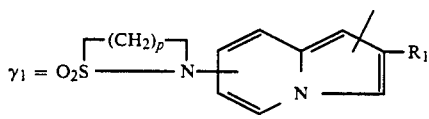

in which Q, R$_1$, R$_4$, X and p are as defined previously, is condensed at a temperature from 90° to 110° C. and in a suitable solvent, for example a polar solvent such as N,N-dimethylformamide, with a compound of general formula:

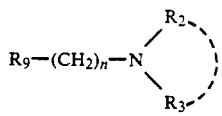

in which R$_2$, R$_3$ and n are as defined previously and R$_9$ represents a halogen atom, a C$_1$-C$_4$ alkylsulfonyloxy radical or a C$_6$-C$_{10}$ arylsulfonyloxy radical, which leads to the formation of the desired compounds of formula I in the form of the free base.

III—When T' represents hydrogen, a nitro group or a

group, R$_4$ represents a —SO$_2$R' group and Y represents a

group, an indole derivative of general formula:

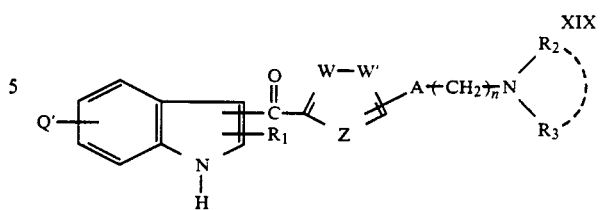

in which A, R$_1$, R$_2$, R$_3$, W, W', Z and n are as defined previously and Q' represents hydrogen, a nitro group or a

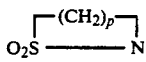

group such as previously defined, is treated in a suitable solvent such as a polar solvent for example N,N-dimethylformamide and in the presence of a basic agent such as an alkali metal hydride or an alkali metal alcoholate with a halide of formula III or IIIa, which leads to the formation of the desired compounds of formula I in the form of the free base.

IV—When T' represents a nitro group, Y represents a

group, A represents —O—, R$_2$, R$_3$, R$_4$ and R'$_4$ are identical and m an n are identical, a ketone derivative of general formula:

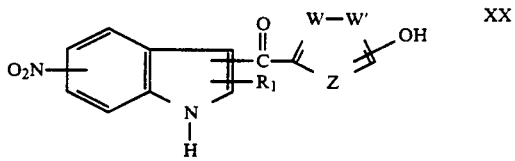

in which R$_1$, W, W' and Z are as defined previously is reacted, in the presence of a basic agent such as an alkali metal hydroxide or carbonate, with a compound of formula XVIII, which leads to the formation of the desired compound of formula I in the form of the free base.

V—When T, T' or T" represents a —NH—SO$_2$R' group, a compound of formula I in which T, T' or T" represents a —N(SO$_2$R')$_2$ group is treated in a suitable solvent such as an alcohol, for example ethanol, with an alkali metal hydroxide, which leads to the formation of the desired compounds of formula I in the form of the free base.

VI—When T or T' represents a

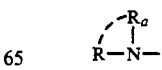

group in which R and R$_a$ are identical and each represents a —SO$_2$R' group, Y represents a

group and A represents a —O— group, a compound of general formula:

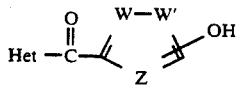    XXI in which W, W' and Z are as defined previously and Het represents a group:

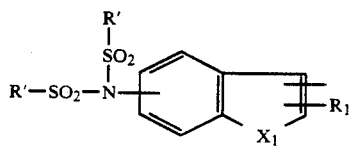

in which $R^1$, $R_1$, and $X_1$ are as defined previously, is reacted in the presence of a basic agent such as an alkali metal hydroxide or carbonate and at the reflux temperature of the medium with a compound of formula XVIII, which leads to the formation of the desired compounds of formula I in the form of the free base.

The compounds of formula I obtained in the form of the free base according to one or other of the methods described above can then be converted into pharmaceutically acceptable salt by reaction with a suitable inorganic or organic acid, for example oxalic, maleic, fumaric, methanesulfonic, benzoic, ascorbic, pamoic, succinic, hexamic, bismethylenesalicyclic, ethanedisulfonic, acetic, propionic, tartaric, salicylic, citric, gluconic, lactic, malic, cinnamic, mandelic, citraconic, aspartic, palmitic, stearic, itaconic, glycolic, p-aminobenzoic, glutamic, benzenesulfonic, p-toluenesulfonic, theophylline acetic acid or with lysine or histidine.

The compounds of formula II as well as the compounds of formula V and XVII in which Het represents a $\alpha_1$ or $\beta_1$ group may be prepared starting from a compound of general formula:

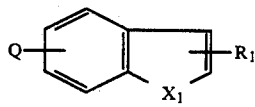    XXII in which Q, $R_1$ and $X_1$ are as defined previously, by reaction, optionally in the presence of a Lewis acid, with a halide of general formula:

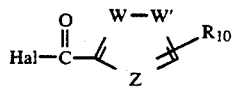    XXIII in which W, W', Z and Hal are as defined previously and $R_{10}$ represents a —OCH$_3$ radical, —A—(CH$_2$)$_n$—Hal or

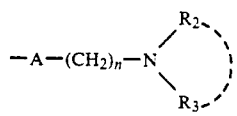

in which A, $R_2$, $R_3$, Hal and n are as defined previously, so as to obtain a ketone of general formula:

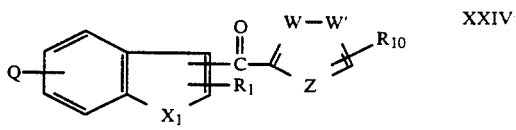    XXIV in which Q, $R_1$, $R_{10}$, $X_1$, W, W' are as defined previously, Usually, the reaction is carried out in the presence of a Lewis acid such as aluminum chloride, stannic chloride or silver trifluoromethanesulfonate. In certain cases, this reaction may be accomplished without the aid of a catalyst, in particular when a compound of formula XXIII is used in which $R_{10}$ represents a

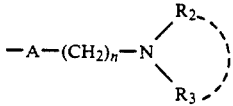

radical.

The ketones of formula XXIV in which Q represents a nitro group and in which $R_{10}$ represents a

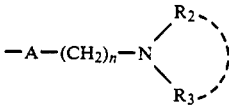

group are compounds of formula II whereas those in which $R_{10}$ represents a —A—(CH$_2$)$_n$—Hal group are in fact compounds of formula V.

The ketones of formula XXIV in which $R_{10}$ represents a —OCH$_3$ radical or —A—(CH$_2$)$_n$—Hal may be used in the following manner:

a) when $R_{10}$ represents a —OCH$_3$ group, O-demethylation is carried out in the presence of a suitable agent such as pyridine hydrochloride, boron tribromide or aluminium chloride in order to produce a ketone derivative corresponding in particular to formula XVII in which Het represents a group of formula $\alpha_1$ or $\beta_1$ or formula XX, which is then condensed in the presence of a basic agent such as an alkali metal hydroxide or carbonate:

either, with an amine of formula XVIII, to produce the compounds of formula II in which A represents —O or, with a dihalogenoalkane of general formula:

    XXV in which Hal and n are as defined previously, in order to produce a compound of formula V in which A represents —O—, then with an amine of formula VI, the reaction taking place in the presence of a basic agent such as an alkali metal hydroxide or carbonate or an excess of the amine of formula VI, which leads to the formation of the compounds of formula II in which A represents —O—.

b) when $R_{10}$ represents a —A—$(CH_2)_n$—Hal group, it is condensed with an amine of formula VI, which leads to the formation of the compounds of formula II in which A represents —O—, —S— or

According to a variant, the compounds of formula XVII or XX may be obtained by direct reaction, in the presence of excess aluminium chloride, between a compound of formula XXII and a halide of formula XXIII in which $R_{10}$ represents a —$OCH_3$ group.

Alternatively, the compounds of formula XXIV in which $R_{10}$ represents a —$OCH_3$ group may be obtained starting from compounds of formula XXII by implementing the various following steps:

a) acetylation by means of acetic anhydride in the presence of aluminium chloride, then bromination in the presence of an alkali metal hydroxide so as to form a carboxylic acid derivative according to the method described in Monatshefte für Chemie 101, pp 1806–1816 (1970) a carboxylic acid derivative which is then reacted with thionyl chloride to give the acyl chlorides of general formula:

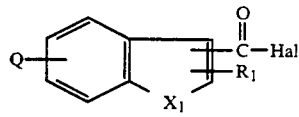
XXVI in which Q, $R_1$, $X_1$ and Hal are as defined previously, b) condensation of the acyl chloride thus formed, in the presence of a Lewis acid such as aluminium chloride or stannic chloride, with an amine of general formula:

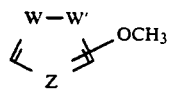
XXVII in which W, W' and Z are as defined previously, which leads to the formation of the desired compounds of formula XXIV.

However, when an excess of aluminium chloride is used in the preceding step b), an O-demethylation also occurs giving rise to the compounds of formula XVII or XX.

The compounds of formula XXVI above include, in particular, compounds of formula XV previously mentioned.

As for the compounds of formula XXII in which Q represents a nitro group, these latter have been described for example in the U.S. Pat. Nos. 3,452,033 or 4,024,273 in J. Org. Chem. 28 p. 2262 (1963), Chem. Abst. 99, 212380, 87, 152014 or 83, 9985, in Ann. Chem. (Rome), 55, p. 1028 (1965) or in J.A.C.S. 75 p. 1877 (1953).

Usually, these compounds may be obtained from a bromobenzyl derivative of general formula:

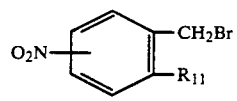
XXVIII in which $R_{11}$ represents a —OH, —SH or —$NH_2$ radical, which is reacted with triphenylphosphine, then cyclised by means of an acyl chloride of general formula:

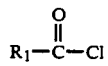
XXIX in which $R_1$ is as defined previously.

This process is applied in particular in the case in which $R_{11}$ represents a —OH radical.

Alternatively, the compounds of formula XXII in which $X_1$ represents —S— may also be obtained by reacting a 2-chloro nitro benzaldehyde with sodium sulfide, then with a chloroketone, followed by reduction of the ketone group of the ketone compound thus formed so as to produce a 2-alkyl nitro benzothiophene.

The compounds of formula XXII in which Q represents a

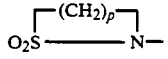

group may be prepared by catalytic hydrogenation, for example in the presence of platinum oxide, of a compound of formula XXII in which Q represents a nitro group, followed by reaction of the amino derivative thus formed with an alkane sultone, which leads to the formation of an aminoalkylsulfonate derivative which is cyclised with phosphorus pentachloride so as to produce the desired compounds.

Compounds of formula V in which Het represents a $\gamma_1$ group may be prepared starting from an indolizine derivative of general formula:

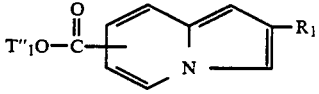
XXX in which $R_1$ and T" are as defined previously, by implementing the following steps:

a) saponification with the aid of an alkali metal hydroxide to obtain a carboxy-indolizine derivative b) reaction of the carboxy-indolizine derivative with ethyl chloroformate in the presence of an amine, then with an alkali metal azide and finally with benzyl alcohol to produce a benzyloxy-carbamoyl-indolizine derivative c) hydrogenation of this benzyl derivative in the presence of a catalyst such as platinum which leads to the formation of an amino-indolizine derivative d) reaction of the amino derivative with an alkane sultone and cyclisation with phosphorus pentachloride e) condensation, in the presence of a Lewis acid such as aluminium chloride, with a halide of formula XXIII in which:

1) $R_{10}$ represents a —A—$(CH_2)_n$—Hal radical to produce the required compounds of formula V 2) $R_{10}$ represents a —$OCH_3$ radical, to produce a compound which is O-demethylated by means of pyridine hydrochloride, boron tribromide or aluminium chloride in order to produce the required compounds of formula XVII.

As for the compounds of formulae XXX and VII, these latter can be obtained by reaction of an ester of 2-methyl pyridine with a bromo-alkanone in order to produce a pyridinium derivative which is cyclised in the presence of triethylamine.

The amines of formulae XVI and XXVII are, for the most part, known compounds since they have been described in U.S. Pat. No. 4,831,054. Usually, these compounds of the formulae XVI and XXVII can be prepared by reacting a compound of general formula:

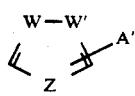  XXXI in which W, W' and Z are as defined previously and A' represents —OH, —SH or —$NH_2$, in the presence of a basic agent such as an alkali metal hydroxide or carbonate with a compound of general formula:

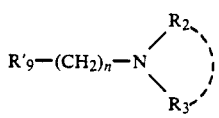  XXXII in which $R_2$, $R_3$ and n are as defined previously and $R'_9$ is such that:
1) when A' represents —OH or —SH, $R'_9$ represents a halogen atom or a $C_1$-$C_4$ alkylsulfonyloxy radical or a $C_6$-$C_{10}$ arylsulfonyloxy radical
2) when A' represents —$NH_2$, $R'_9$ represents a

radical in which $R''_9$ represents a halogen atom.

The compounds of formula XIX are either compounds of formula I above, or compounds which have been described in Eur. J. Med. Chem. Chimica Therapeutica, 12, No. 5 pp. 483-487 (1977).

These latter can be prepared by known methods, in particular by the application of methods similar to those previously described.

The compounds of formula XXI can be obtained starting from an amino compound of general formula:

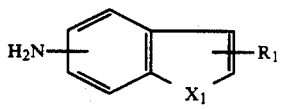  XXXIII in which $R_1$ and $X_1$ are as defined previously, by implementing the following process:
a) reaction with two equivalents of a compound of formula III or IIIa in the presence of an acid acceptor such as an amine, for example triethylamine,
b) condensation of the bisulfonamido derivative obtained with a compound of formula XXIV in which $R_{10}$ represents a —$OCH_3$ group in the presence of a Lewis acid such as tin tetrachloride, c) demethylation by means of a suitable agent such as boron tribromide in order to form the desired compounds of formula XXI.

The compounds of formula XXXIII can be prepared by hydrogenation of a derivative of formula XXII, in which Q represents a nitro group, in the presence of platinum or palladium oxide.

As for the compounds of formulae VI, VIII, XII, XXIII, XXV, XXVIII, XXXI and XXXII, they are known compounds. Most of them have been published in particular in the U.S. Pat. Nos. 4,024,273 and 4,831,054, the patent applications EP 0235.111 or WO 90/02743 or in Eur. J. Med. Chem.-Chimica Therapeutica 12, No. 5 pp. 483-487 (1977). These compounds can all be prepared by known methods.

At present, it is undoubtedly of interest to use as agent for the prevention of cardiac arrhythmias, the potentialities offered by delayed conduction of the electrical impulse at the cardiac cell or the prolongation of the refractory period.

Although many physio-pathological states prolong the repolarization of the cardiac cell and are associated with a reduced incidence of cardiac fibrillation, the concept of pharmacological control of rhythmic disorders by increasing the action potential is relatively new.

The action potential of the myocardiac cell in fact represents a modification of the resting potential of this cell which, after having attained the threshold potential (−70 millivolts) sufficiently rapidly, initiates a sequence of changes in the membrane potential.

After passage of the impulse, the myocardium remains transiently insensitive to a new stimulation; during the absolute refractory period it is absolutely impossible to excite the myocardium whereas during the relative refractory period a sufficiently powerful stimulus can lead to a slowly propagated response. The existence of the refractory periods determines the unidirectional nature of the propagation of the impulse.

The characteristics of the action potential determine those of the conduction and the refractory periods. Consequently, any shortening of the repolarization is arrhythmogenic as a result of the concomitant shortening of the refractory period. Conversely, any interference uniformly lengthening the action potential produces a lengthening of the absolute refractory period and this diminishes the arythmogenicity.

In other words, if the attainment of a threshold level of the membrane potential necessary to generate a second action potential is delayed, in response to a stimulus, by interfering in processes which normally control the rate of repolarization, the refractory periods (absolute period and efficacious period) of the cardiac muscle ought to be correspondingly prolonged, a phenomenon which would be expected to create an antiarrhythmic mechanism.

At present, amiodarone or 2-n-butyl 3-[4-(2-diethylamino ethoxy) 3,5-diiodo benzoyl] benzofuran is one of the rare anti-arrhythmic agents on the market which possesses the properties just explained.

The compound, in fact, prolongs the repolarization plateau without modifying the rate of rapid depolarization. Its anti-arrhythmic effect derives from the uniform lengthening of the action potentials and the refractory periods of the myocardial cells.

Furthermore, amiodarone possesses incomplete antiadrenergic properties of the α and β types. Hence, this compound may be considered not as a β blocker but as an adreno-decelerator, i.e. as a partial antagonist of α and β adrenergic reactions. Such properties are of indisputable benefit since it appears desirable not to look for complete α or β antagonistic properties in view of the side effects to which they may lead in the clinic ("Bruxelles Médical", No. 9, September 1969, pages 543–560).

Derivatives of benzofuran, benzothiophene, indole or indolizine with chemical structures similar to that of amiodarone are already known, i.e. those bearing a dialkylamino- or monoalkylamino-alkoxy-benzoyl chain at position 3: such compounds exhibited active properties on the cardiovascular system to varying degrees.

In this context, the U.S. Pat. Nos. 3,920,707 and 3,947,470, the EP patent applications Nos. 338.746 and 360.784, the PCT patent applications Nos. WO 89/02888, 89/02892 and 89/02893 as well as Eur. J. Med. Chem.-Chimica Therapeutica 12, No. 5 p. 483–487 (1977) may be mentioned.

Now at present, there appears to exist no known derivative of benzofuran, benzothiophene or indole which bears the dialkylamino- or monoalkylamino-alkoxybenzoyl chain and which is substituted on the homocycle by a substituted or unsubstituted amino group.

Although the U.S. Pat. No. 3,947,470 covers adequately nitrogenous derivatives of the homocycle, i.e. derivatives bearing a nitro group, no compound of this type may be considered as having been actually prepared and still less tested from a pharmacological point of view.

The surprising discovery has now been made in the context of the invention that derivatives of benzofuran, benzothiophene, indole and indolizine bearing a monoalkylamino- or dialkylamino-alkoxy-benzoyl chain as well as other groups attached to the heterocycle and particularly to the homocycle of benzofuran, benzothiophene or indole or to the pyridine moiety of indolizine possess remarkable pharmacological properties which are expressed in particular by an increase in the duration of the action potential and the refractory periods of the cardiac cell.

These properties have even shown themselves to be superior to those recorded with known derivatives or with analogues bearing a nitro substituent on the homocycle.

Furthermore, it has been possible to demonstrate that compounds of the invention possess fewer possible side effects than analogous known compounds.

In particular, it is known that amiodarone causes phospholipidoses in the lung, which results in the destruction of macrophages in the alveoli. This destruction is expressed in the patient undergoing treatment with amiodarone by the appearance of pulmonary complications, such as respiratory insufficiency which will require the cessation of treatment.

Other known compounds such as 2-n-butyl 3-[4-(3-di-n-butylamino-propoxy)benzoyl] benzofuran, also exhibit this side effect. For example, it has been possible to demonstrate that at an oral dose of 139 mg/kg for 14 days this compound causes an 11.6% increase of the pulmonary phospholipids in the rat. Under the same conditions, at a dose of 100 mg/kg, amiodarone causes a 26.7% increase in the level of phospholipids in the lung.

In contrast, the following compounds of the invention:

2-n-butyl 3-[4-(3-di-n-butylamino-propoxy)benzoyl] 5-methylsulfonamido benzofuran (Ex. 2)

5-amino 3-[4-(3-di-n-butylamino-propoxy)benzoyl] 2-n-butyl benzofuran (Ex. 3)

do not alter the levels of pulmonary phospholipids at doses of 116 mg/kg and 135 mg/kg, respectively.

In view of this absence of pulmonary lipidoses and in the light of other pharmacological tests performed, the compound of the invention which showed the best potentialities as anti-arrhythmic and antiadrenergic agent is 2-n-butyl 3-[4-(3-di-n-butylamino-propoxy) benzoyl] 5-methylsulfonamido benzofuran and its pharmaceutically acceptable salts.

The results of pharmacological tests performed for the purpose of determining the properties of the compounds of the invention on the cardiovascular system are listed below.

I—Effect on the duration of the action potential

The effect of the compounds of the invention on the duration of the action potential has been demonstrated by the measurement of the effect of intravenous administration in the rat "in vivo".

The following procedure is used.

Sprague-Dawley male rats weighing 250 to 450 g are anaesthetized and attached to a carrier in the dorsal position. After bipolar electrodes have been attached to the 4 paws for the recording of the electrocardiogram, the rat is placed under artificial respiration. After thoracotomy and rupture of the pericardium, a suction electrode is applied to the heart (while avoiding the coronary arteries). This latter adheres instantaneously as a result of the force of aspiration of a vacuum pump to which it is connected.

The action potential and the electrocardiogram are then recorded simultaneously at a rate of 200 mm/sec before the administration of a test compound as well as at different times (1, 3, 5 and 10 minutes) after the administration of a dose of a test compound during 30 seconds.

The results obtained are expressed in % increase of the duration of the action potential (D.A.P.) relative to the duration recorded before the administration of the test substance, the duration being measured at 90% of the amplitude of the action potential.

The following examples illustrate the results obtained, the compounds of formula I being in the form of the free base or a salt.

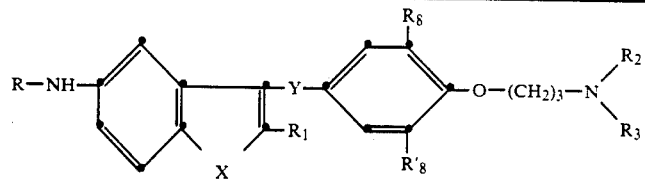

| Y | X | R | R₁ | R₂ | R₃ | R₈ R'₈ | Dose (mg/kg) | ↑ D.A.P. |
|---|---|---|---|---|---|---|---|---|
| $\overset{O}{\underset{C}{\|}}$ | O | CH₃SO₂— | n-C₄H₉ | n-C₄H₉ | n-C₄H₉ | H | 10 | 60 |
| $\overset{O}{\underset{C}{\|}}$ | O | CH₃SO₂— | n-C₄H₉ | H | —C(CH₃)₃ | H | 10 | 32 |
| $\overset{O}{\underset{C}{\|}}$ | O | H | n-C₄—H₉ | CH₃ | —(CH₂)₂—C₆H₃(OCH₃)₂ | H | 10 | 51 |
| $\overset{O}{\underset{C}{\|}}$ | O | CH₃SO₂— | n-C₄H₉ | CH₃ | —(CH₂)₂—C₆H₃(OCH₃)₂ | H | 10 | 70 |
| $\overset{O}{\underset{C}{\|}}$ | O | H | n-C₄H₉ | n-C₄H₉ | n-C₄H₉ | CH₃ | 5 | 57 |
| $\overset{O}{\underset{C}{\|}}$ | O | CF₃SO₂— | n-C₄H₉ | n-C₄H₉ | n-C₄H₉ | H | 0.1 | 63 |
| $\overset{O}{\underset{C}{\|}}$ | O | CH₃SO₂— | (furyl/phenyl ring) | n-C₄H₉ | n-C₄H₉ | H | 10 | 65 |
| $\overset{O}{\underset{C}{\|}}$ | O | CH₃SO₂— | iso-C₃H₇ | n-C₄H₉ | n-C₄H₉ | H | 10 | 60 |
| $\overset{O}{\underset{C}{\|}}$ | O | CH₃—C₆H₄—SO₂— | n-C₄H₉ | n-C₄H₉ | n-C₄H₉ | H | 10 | 37 |
| $\overset{OH}{\underset{CH}{\|}}$ | O | CH₃SO₂— | n-C₄H₉ | n-C₄H₉ | n-C₄H₉ | H | 10 | 24 |
| $\overset{O}{\underset{C}{\|}}$ | NH | CH₃SO₂— | n-C₄H₉ | n-C₄H₉ | n-C₄H₉ | H | 10 | 42 |
| $\overset{O}{\underset{C}{\|}}$ | NCH₃ | H | n-C₄H₉ | n-C₄H₉ | n-C₄H₉ | H | 10 | 83 |
| $\overset{O}{\underset{C}{\|}}$ | NH | H | n-C₄H₉ | n-C₄H₉ | n-C₄H₉ | H | 10 | 42 |
| —CH₂— | O | CH₃SO₂ | n-C₄H₉ | n-C₄H₉ | n-C₄H₉ | H | 10 | 38 |

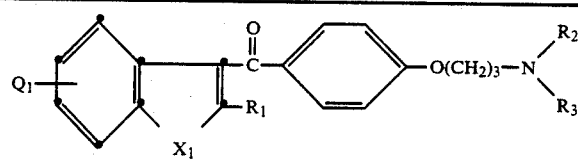

| X₁ | Q₁ | R₁ | R₂ | R₃ | Dose (mg/kg) | ↑ D.A.P. |
|---|---|---|---|---|---|---|
| O | (CH₃SO₂)₂N-7 | CH₃ | n-C₄H₉ | n-C₄H₉ | 5 | 80 |
| O | NH₂-7 | CH₃ | n-C₄H₉ | n-C₄H₉ | 10 | 73 |
| O | CH₃SO₂N-7 | CH₃ | n-C₄H₉ | n-C₄H₉ | 10 | 140 |

-continued

| | | | | | |
|---|---|---|---|---|---|
| O<br>O₂S—N-7 (ring) | | n-C₄H₉ | n-C₄H₉ | n-C₄H₉ | 10 | 70 |
| \N—(CH₂)₃—N(C₄H₉)₂ | NO₂-5 | n-C₄H₉ | n-C₄H₉ | n-C₄H₉ | 10 | 42 |
| \N—SO₂CH₃ | H | n-C₄H₉ | n-C₄H₉ | n-C₄H₉ | 10 | 77 |

| $X_1$ | $Q_1$ | $R_1$ | $R_2$ | $R_3$ | Dose (mg/kg) | ↑ D.A.P. |
|---|---|---|---|---|---|---|
| O | NH₂-5 | CH₃ | n-C₄H₉ | n-C₄H₉ | 10 | 77 |
| S | NH₂-5 | n-C₄H₉ | CH₃ | —(CH₂)₂—C₆H₃(OCH₃)₂ | 10 | 35 |
| S | CH₃SO₂-5 | n-C₄H₉ | CH₃ | —(CH₂)₂—C₆H₃(OCH₃)₂ | 10 | 33 |
| \NH | NO₂-5 | n-C₄H₉ | n-C₄H₉ | n-C₄H₉ | 10 | 64 |

| $Q_2$ | $R_1$ | $R_2$ | $R_3$ | Dose (mg/kg) | ↑ D.A.P. |
|---|---|---|---|---|---|
| H₅C₂O—C(O)— | phenyl | n-C₄H₉ | n-C₄H₉ | 10 | 52 |
| HOC(O)— | n-C₄H₉ | n-C₄H₉ | n-C₄H₉ | 1 | 13 |
| C₆H₅—CH₂—O—C(O)—NH— | n-C₄H₉ | n-C₄H₉ | n-C₄H₉ | 10 | 22 |
| NH₂ | n-C₄H₉ | n-C₄H₉ | n-C₄H₉ | 10 | 53 |
| CH₃SO₂— | n-C₄H₉ | n-C₄H₉ | n-C₄H₉ | 10 | 66 |
| CH₃—NH—C(O)— | n-C₄H₉ | n-C₄H₉ | n-C₄H₉ | 10 | 23 |

-continued

| | | | | | |
|---|---|---|---|---|---|
| 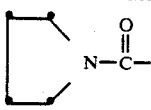 | n-C4H9 | n-C4H9 | n-C4H9 | 10 | 52 |

For comparative purposes, the following results were obtained with the known compound:

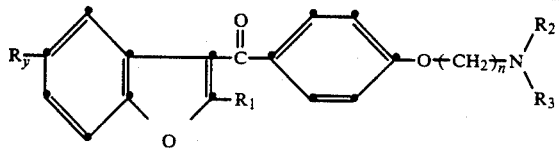

| $R_y$ | $R_1$ | $R_2$ | $R_3$ | n | Dose (mg/kg) | ↑ D.A.P. (%) |
|---|---|---|---|---|---|---|
| H | n-C4H9 | n-C4H9 | n-C4H9 | 3 | 10 | 31 |

These results show the marked superiority of the compounds of the invention compared with the known compound as agents capable of increasing the duration of the action potential of the myocardial cell.

II—Antiadrenergic properties

The purpose of this test is to determine the capacity of the compounds of the invention to reduce the increase in blood pressure induced by epinephrine (anti-α effect) and the acceleration of cardiac frequency induced by isoprenaline (anti-β effect) in the dog anaesthetized beforehand with pentobarbital and atropine.

The dose of epinephrine which causes a reproducible increase in the arterial blood pressure of about $133.10^2$Pa (between 3 and 10 μg/kg) and the dose of isoprenaline which causes a reproducible increase in cardiac frequency of about 70 beats/minute (1 to 2 μg/kg) are first determined for each dog. Every ten minutes the doses of epinephrine and isoprenaline thus determined are injected alternately and after two successive reference responses have been obtained, a quantity of the test compound is administered intravenously.

Anti-α effect

The reduction of the hypertension caused by the test compound is recorded as a percentage of the reference hypertension previously obtained (about 100 mm Hg).

Anti-β effect

The reduction of the acceleration of the cardiac frequency caused by the test compound is recorded as a percentage of the reference tachycardia previously measured (about 70 beats).

In both cases, the results of the reduction of arterial pressure and of cardiac frequency are expressed as follows:
+ for a reduction <50%
++ for a reduction ≧50%
+++ for a sub-total reduction (almost complete reduction)

The following results were recorded:

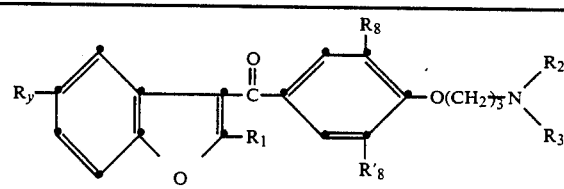

| | | | | | | Effect | |
|---|---|---|---|---|---|---|---|
| $R_y$ | $R_1$ | $R_2$ | $R_3$ | $R_8$ et $R'_8$ | Dose (mg/kg) | anti-α | anti-β |
| CH3SO2NH— | n-C4H9 | n-C4H9 | n-C4H9 | H | 10 | +++ | +++ |
| CH3SO2NH— | n-C4H9 | n-C4H9 | n-C4H9 | CH3 | 6,5 / 5 | +++ | +++ |
| NH2 | n-C4H9 | n-C4H9 | n-C4H9 | CH3 | 5,7 | +++ | +++ |
| (CH3SO2)2N— | n-C4H9 | n-C4H9 | n-C4H9 | H | 5 | +++ | ++ |

For the purposes of comparison the results obtained with known compounds are presented below:

| | | | | | | | |
|---|---|---|---|---|---|---|---|
| H | n-C4H9 | H | n-C4H9 | H | 10 | (+) | + |
| H | n-C4H9 | n-C4H9 | n-C4H9 | CH3 | 10 | ++ | ++ |

III— Toxicity

The toxicity of the compounds of the invention is found to be compatible with their use in therapy.

The therapeutic compositions according to the invention may be made available in any form suitable for administration in human and veterinary therapy. As regards the dosage unit, this latter may take the form, for example, of a tablet, a sugar-coated tablet, a capsule, a gelatine capsule, a powder, a suspension or a syrup for oral administration, a suppository for rectal administration and a solution or suspension for parenteral administration.

The dosage units of the therapeutic compositions of the invention may comprise, for example, from 50 to 500 mg by weight of the active ingredient for oral administration, from 50 to 200 mg of active ingredient for rectal administration and from 50 to 150 mg of active ingredient for parenteral administration.

Depending on the route of administration selected, the therapeutic or veterinary compositions of the invention will be prepared by combining at least one of the compounds of formula I or a non-toxic addition salt of this compound with a suitable excipient, which latter may be constituted for example by at least one ingredient selected from the following substances: lactose, starches, talc, magnesium stearate, polyvinylpyrrolidone, alginic acid, collodal silica, distilled water, benzyl alcohol or sweetening agents.

The following non-limiting examples illustrate the preparation of the compounds and the compositions of the invention:

EXAMPLE 1

Preparation of 5-amino 3-[4-(3-di-n-butylamino-propoxy)benzoyl] 2-n-butyl benzofuran (SR 33580)

a) 2-hydroxy 5-nitro benzyltriphenylphosphonium bromide 100 g (0.43 mole) of 2-hydroxy 5-nitrobenzyl bromide and 113 g (0.43 mole) of triphenylphosphine are heated at reflux for 0.5 hour in 1600 ml of chloroform. The mixture is allowed to cool and the white precipitate formed is filtered off. The filtrate is evaporated to dryness in a vacuum and the residue is taken up in 500 ml of toluene. The precipitate is filtered off, washed with toluene and the solids formed are pooled and dried in a vacuum at 50° C.

In this manner, 210.5 g of 2-hydroxy 5-nitrobenzyl triphenylphosphonium, bromide are obtained.
Yield: 99.01% b) 2-n-butyl 5-nitro benzofuran 113.5 g (0.94 mole) of pentanoyl chloride are added slowly with stirring to a mixture of 370 g (0.75 mole) of 2-hydroxy 5-nitrobenzyltriphenylphosphonium, bromide and 120.2 g (1.52 mole) of pyridine in 700 ml of chloroform. The mixture is heated at reflux for 2 hours. 2800 ml of toluene are added and 1400 ml of solvents are distilled. 228 g (2.28 moles) of triethylamine are then added and the mixture is heated at reflux for 3 hours. It is allowed to cool, the triphenylphosphine-oxide, formed is filtered off, washed with ethyl acetate and the filtrate is concentrated in a vacuum. The viscous residue obtained is dissolved in acetonitrile and extracted with pentane in a liquid-liquid, extraction apparatus. The solution is dried over sodium sulfate, filtered and evaporated to dryness.

In this manner, crude 2-n-butyl 5-nitro-benzofuran is obtained.
Purity [high performance liquid chromatography (HPLC)]: 97.9%
B.p. 120°–123° C. (0.02 mm Hg or 2.66 Pa).

The following compounds were prepared in a manner similar to that previously described:
2-methyl 5-nitro-benzofuran
M.p.: 96° C. (isopropyl ether)
Purity (HPLC): 100%
2-ethyl 5-nitro benzofuran
M.p.: 86° C. (isopropanol)
Purity (HPLC): 99.8%
2-n-propyl 5-nitro benzofuran
M.p.: 38° C. (isopropanol)
Purity (HPLC): 99%
2-isopropyl 5-nitro benzofuran
M.p.: 73° C. (isopropyl ether)
Purity (HPLC): 99.45%
2-phenyl 5-nitro benzofuran
M.p.: 159° C. (isopropyl ether)
Purity (HPLC): 99.5% c) 2-n-butyl 3-(4-methoxy benzoyl) 5-nitro benzofuran 59.8 ml (0.50 mole) of tin tetrachloride are added gradually to a solution of 44.5 g (0.2 mole) of 2-n-butyl 5-nitro benzofuran and 44.3 g (0.26 mole) of anisoyl chloride in 308 ml of dichloroethane. The temperature is maintained at 23° C. and stirring is continued for 24 hours. The mixture is poured onto 770 ml of ice-water and extracted 3 times with 150 ml of dichloroethane. The solution is washed with water, 5% sodium hydrogen carbonate solution and again with water. It is evaporated to dryness and the product thus obtained crystallizes rapidly [purity on high performance liquid chromatography (HPLC): 91.69%]. It is recrystallized from 250 ml of isopropanol and 59 g of 2-n-butyl 3-(4-methoxy benzoyl) 5-nitro benzofuran are thus obtained.
Yield: 83.5%
Purity (HPLC): 96.39%
M.p.: 95° C.

The following compounds were prepared by following a similar process to the process just described:
3-(4-methoxy benzoyl) 2-methyl 5-nitro benzofuran
M.p.: 167° C. (methyl ethyl ketone)
Purity (HPLC): 99.9%
2-isopropyl 3-(4-methoxy benzoyl) 5-nitro benzofuran
Oil
Purity (HPLC): 99.6%
3-(4-methoxy benzoyl) 5-nitro 2-phenyl benzofuran
M.p.: 153° C. (methyl ethyl ketone)
Purity (HPLC): 99.8%
3-(4-methoxy benzoyl) 2-ethyl 5-nitro benzofuran
M.p.: 130° C. (methanol)
Purity (HPLC): 99.5%
3-(4-methoxy benzoyl) 5-nitro 2-propyl benzofuran
M.p.: 73° C. (methanol)
Purity (HPLC): 99.1%
2-(4-methoxy benzoyl) 3-methyl 5-nitro benzofuran
M.p.: 180° C.
Purity (HPLC): 99.02%
3-(4-methoxy benzoyl) 2-methyl 7-nitro benzofuran
M.p.: 130°–132° C.
Purity (HPLC): 98.32%
2-(4-methoxy benzoyl) 3-n-butyl 5-nitro indole
M.p.: 142° C. (heptane/ethyl acetate)
2-(4-methoxy benzoyl) 3-n-butyl 1-methyl 5-nitro indole
M.p.: 102° C. (ethanol)
3-(4-methoxy benzoyl) 2-ethyl 1-methyl 4-nitro indole
M.p.: 136° C. (heptane/isopropanol 6/4)

d) 2-n-butyl 3-(4-hydroxy benzoyl) 5-nitro benzofuran 69.7 g (0.20 mole) of 2-n-butyl 3-(4-methoxy benzoyl) 5-nitro benzofuran are heated at reflux for 20 hours in 510 ml of dichloroethane in the presence of 60 g (0.45 mole) of aluminium chloride. After reaction, the mixture is allowed to cool, poured onto 510 ml of ice-water, filtered, the organic phase is washed to neutrality and the product ultimately obtained is dried in a vacuum at 50° C.

In this manner, 61.2 g of 2-n-butyl 3-(4-hydroxy benzoyl) 5-nitro benzofuran are obtained.
Yield: 90.1%
Purity (HPLC): 99.19%
M.p.: 121° C.

The following compounds were prepared by following the same process as that described above:
3-(4-hydroxy benzoyl) 2-methyl 5-nitro benzofuran
M.p.: 182° C. (isopropanol)
Purity (HPLC): 99.7%
3-(4-hydroxy benzoyl) 2-isopropyl 5-nitro benzofuran
M.p.: 132° C.
Purity (HPLC): 99.9%
3-(4-hydroxy benzoyl) 5-nitro 2-phenyl benzofuran M.p.: 207° C. (chloroform)
Purity (HPLC): 100%

2-ethyl 3-(4-hydroxy benzoyl) 5-nitro benzofuran
M.p.: 152° C. (dichloroethane)
Purity (HPLC): 99.4%

3-(4-hydroxy benzoyl) 5-nitro 2-n-propyl benzofuran
M.p.: 119° C. (toluene)
Purity (HPLC): 98.8%

2-(4-hydroxy benzoyl) 3-methyl 5-nitro benzofuran
M.p.: 235° C. (methanol)
Purity (HPLC): 96.19%

3-(4-hydroxy benzoyl) 2-methyl 7-nitro benzofuran
M.p.: 201° C. (methyl ethyl ketone)
Purity (HPLC): 98.51% e) 2-n-butyl 3-[4-(3-di-n-butylamino-propoxy)benzoyl] 5-nitro benzofuran

A mixture consisting of 11.9 g (0.035 mole) of 2-n-butyl 3-(4-hydroxy benzoyl) 5-nitro benzofuran and 4.8 g (0.035 mole) of potassium carbonate in 60 ml of methyl ethyl ketone is stirred for 0.5 hour. 7.2 g (0.035 mole) of 1-chloro 3-di-n-butylamino propane are then added and the mixture is heated at reflux for 20 hours. It is allowed to cool, the salts formed are filtered off, washed with methyl ethyl ketone and the filtrate is evaporated to dryness. The residue is dissolved in 250 ml of ethyl ether and the solution is washed twice with 500 ml of 5% sodium hydroxide. It is washed with water, dried over sodium sulfate, filtered and decolorized with active charcoal. It is filtered and the filtrate is evaporated.

In this manner, 15.8 g of 2-n-butyl 3-[4-(3-di-n-butyl aminopropoxy)benzoyl] 5-nitro benzofuran are obtained.

Yield: 88.76%
Purity (HPLC): 98.25%
M.p. (oxalate): 84° C. (ether/isopropanol).

The following compounds were obtained by following the process similar to that described above:

3-[4-(3-di-n-butylamino-propoxy)benzoyl] 5-nitro 2-methyl benzofuran.
M.p.: 63° C. (isopropyl ether)
Purity (HPLC): 98.9%

3-[4-(3-tert.butylamino propoxy)benzoyl] 2-n-butyl 5-nitro benzofuran
M.p. (acid oxalate): 244° C. (acetone/methanol)

3-{4-[3-(N-methyl N-3,4-dimethoxy-β-phenethyl) amino-propoxy]benzoyl} 5-nitro 2-n-butyl benzofuran
M.p.: (acid oxalate): 114° C. (acetone)

3-[4-(3-di-n-butylamino-propoxy)benzoyl] 2-ethyl 5-nitro benzofuran
M.p. (hydrochloride): 139° C. (ethyl acetate)
Purity (HPLC): 99.6%

3-[4-(3-di-n-butylamino-propoxy)benzoyl] 5-nitro 2-n-propyl benzofuran
M.p.: 126° C. (ethyl acetate)
Purity (HPLC): 97.9%

2-n-butyl 3-[4-(3-diethylamino-propoxy)benzoyl] 5-nitro benzofuran
M.p. (hydrochloride): 131° C. (ethyl acetate)
M.p. (hydrochloride): 131° C. (ethyl acetate)
Purity (HPLC): 98.4%

3-[4-(3-di-n-butylamino-propoxy)benzoyl] 2-methyl 7-nitro benzofuran
M.p. (toluenesulfonate): 118° C. (ethyl acetate)
Purity (HPLC): 99.44%

2-[4-(3-di-n-butylamino-propoxy)benzoyl]3-methyl 5-nitro benzofuran
M.p. (acid fumarate): 148° C. (ethyl acetate)
Purity (HPLC): 99.8%

3-[4-(3-di-n-butylamino-propoxy)benzoyl] 5-nitro 2-isopropyl benzofuran
Oil
Purity (HPLC): 99%

3-[4-(3-di-n-butylamino-propoxy)benzoyl] 5-nitro 2-phenyl benzofuran
M.p.: 95° C. (isopropyl ether)
Purity (HPLC): 98.5% f) 5-amino 3-[4-(3-di-n-butylamino-propoxy)benzoyl] 2-n-butyl benzofuran 20.4 g (0.04 mole) of 2-n-butyl 3-[4-(3-di-n-butylamino-propoxy)benzoyl] 5-nitro benzofuran are stirred in 200 ml of ethanol in the presence of 0.6 g of platinum oxide in a hydrogenation apparatus under a pressure of 3.4 atmospheres ($3.44 \times 10^5$ Pa) of hydrogen. When the pressure attains 2.7 atm ($2.73 \times 10^5$ Pa), the reaction is complete and this requires about 20 minutes.

In this manner, 5-amino 3-[4-(3-di-n-butylamino-propoxy) benzoyl] 2-n-butyl benzofuran are obtained in a yield of 98.4%.
Purity (HPLC): 95.28%

EXAMPLE 2

Preparation of 5-amino 3-[4-(3-di-n-butylamino-propoxy)benzoyl] 2-methyl benzofuran dioxalate A solution of oxalic acid in diethyl ether is added to a solution of 5-amino 3-[4-(3-di-n-butylamino-propoxy)-benzoyl] 2-methyl benzofuran in diethyl ether. The product is filtered off and recrystallized from methanol.

In this manner, 5-amino 3-[4-(3-di-n-butylamino-propoxy) benzoyl] 2-methyl benzofuran dioxalate is obtained.
M.p.: 136° C.
Purity (HPLC): 99.3%

EXAMPLE 3

Preparation of 2-n-butyl 3-[4-(3-di-n-butylamino-propoxy)benzoyl] 5-methylsulfonamido benzofuran hydrochloride (SR 33589B)

a) 2-n-butyl 3-[4-(3-di-n-butylamino-propoxy) benzoyl] 5-methylsulfonamido benzofuran A solution of 17.6 g (0.154 mole) of methanesulfonyl chloride in 375 ml of dichloroethane is added dropwise to a solution of 68.3 g (0.15 mole) of 5-amino 3-[4-(3-di-n-butylamino-propoxy) benzoyl] 2-n-butyl benzofuran and 23.6 g (0.23 mole) of triethylamine in 750 ml of dichloroethane. The mixture is stirred for 20 h and poured into 500 ml of water. The phases are separated, the organic phases washed with water and evaporated to dryness. The crude product thus obtained (79.5 g; crude yield: 100%) is then purified by elution chromatography on a column of silica (eluant: ethyl acetate).

In this manner, 48 g of purified 2-n-butyl 3-[4-(3-di-n-butylamino-propoxy)benzoyl] 5-methylsulfonamido benzofuran are recovered.
Yield: 61.6%.

Treatment of the product thus obtained with hexane gave 44 g of a crystalline fraction (purity by HPLC:

96.1%) and 4 g of a crystalline fraction (purity by HPLC: 99%)

M.p.: 65.3°C b) 2-n-butyl 3-[4-(3-di-n-butylamino-propoxy)benzoyl] 5-methylsulfonamido benzofuran hydrochloride 2 g of 2-n-butyl 3-[4-(3-di-n-butylamino-propoxy)-benzoyl] 5-methyl sulfonamido benzofuran are dissolved in 40 ml of anhydrous ethyl acetate.

Hydrogen chloride in ether is added with stirring to pH=3. After a few minutes, the hydrochloride begins to precipitate. It is filtered off after 0.75 hour to give 2.03 g of a colourless product.

In this manner, 2-n-butyl 3-[4-(3-di-n-butylamino-propoxy) benzoyl] 5-methylsulfonamido benzofuran hydrochloride is recovered.

M.p.: 143° C. (acetone)

EXAMPLE 4

Preparation of 5-amino 2-n-butyl 3-[4-(2-di-n-butylamino-ethoxy) benzoyl] benzofuran dioxalate a) 3-[4-(2-bromoethoxy)benzoyl] 2-n-butyl 5-nitro benzofuran A mixture consisting of 23.22 g (0.06 mole) of 2-n-butyl 3-(4-hydroxy benzoyl) 5-nitro benzofuran and 10 g (0.07 mole) of finely ground anhydrous potassium carbonate is stirred for 0.5 h in 400 ml of methyl ethyl ketone. 45 g (0.24 mole) of 1,2-dibromo ethane are then added and the mixture is refluxed for 6 h. It is allowed to cool, the mineral salts are filtered off, washed with acetone and the filtrate is evaporated to dryness in a vacuum. The crude product obtained is purified by elution chromatography on a column of silica (eluant: toluene).

In this manner, 15 g of 3-[4-(2-bromo ethoxy)benzoyl] 2-n-butyl 5-nitro benzofuran are obtained after recrystallization from pentane.

Yield: 56%
M.p.: 81° C.
Purity (HPLC): 95.2%

The following compounds were prepared by following the same procedure as that described above:

3-[4-(5-bromopentoxy)benzoyl] 2-n-butyl 5-nitro benzofuran

M.p.: 55° C. (pentane)
Purity (HPLC): 98%

3-[4-(3-bromopropoxy)benzoyl] 2-n-butyl 5-nitro benzofuran

Purity (HPLC): 91.28% b) 2-n-butyl 3-[4-(2-di-n-butylamino-ethoxy)benzoyl] 5-nitro benzofuran hydrochloride A mixture consisting of 15 g (0.0336 mole) of 3-/4-(2-bromoethoxy)benzoyl/2-n-butyl 5-nitro benzofuran, 17.3 g (0.134 mole) of di-n-butylamine and 18.5 g (0.134 mole) of anhydrous potassium carbonate is refluxed for 3 days in 200 ml of toluene. The mixture is allowed to cool, poured into water and the organic phase is separated. The aqueous phase is extracted 3 times with 50 ml of toluene; the organic phases are pooled and washed with water. It is dried over sodium sulfate, filtered and evaporated to dryness in a vacuum. The residue is then purified by elution chromatography on a column of silica (eluants: hexane/ethyl acetate 8/2) to give 12.7 g (yield: 76.4%) of the desired compound in the form of the free base. The hydrochloride is formed in ethyl ether and recrystallized from ethyl acetate.

In this manner, 2-n-butyl 3-[4-(2-di-n-butylamino-ethoxy) benzoyl] 5-nitro benzofuran hydrochloride is obtained M.p.: 119.5° C.
Purity (HPLC):100%

The following compounds were obtained by following the process similar to that described above:

2-n-butyl 3-[4-(5-di-n-butylamino-pentoxy)benzoyl] 5-nitro benzofuran acid oxalate M.p.: 106.7° C. (isopropanol)
Purity (HPLC): 99.6%

2-n-butyl 3-[4-(3-n-butylamino-propoxy)benzoyl] 5-nitro benzofuran

Oil
Purity (HPLC): 97.8% c) 5-amino 2-n-butyl 3-[4-(2-di-n-butylamino-ethoxy) benzoyl] benzofuran dioxalate This compound was obtained according to the method described in Example 1f.

M.p.: 155° C. (isopropanol)
Purity (HPLC): 96%

EXAMPLE 5

Preparation of 3-[4-(3-di-n-butylamino-propoxy)benzoyl] 5-bismethylsulfonamido 2-ethyl benzofuran A solution of 7.56 g (0.066 mole) of methanesulfonyl chloride in 40 ml of carbon tetrachloride is added dropwise to a solution of 10 g (0.022 mole) of 5-amino 3-[4-(3-di-n-butylamino-propoxy)benzoyl] 2-ethyl benzofuran and 22.45 g (0.22 mole) of triethylamine in 200 ml of carbon tetrachloride. The mixture is refluxed for 20 h, poured into a mixture of ice and water, then the organic phase is separated. It is washed with water, dried over sodium sulfate, filtered and evaporated to dryness in a vacuum. The residue is then purified by elution chromatography on a column of silica (eluant: ethyl acetate), then the crude product obtained is recrystallized from heptane.

In this manner, 8.4 g of 3-[4-(3-di-n-butylamino-propoxy)benzoyl] 5-bismethylsulfonamido 2-ethyl benzofuran are obtained Yield: 63%
M.p.: 70%
Purity (HPLC): 98.2%

EXAMPLE 6

Preparation of 3-[4-(2-di-n-butylamino-ethoxy)benzoyl] 2-n-butyl 5-methylsulfonamido benzofuran (SR 34488)

A mixture consisting of 6.2 g (0.01 mole) of 3-(2-di-n-butylamino-ethoxy) benzoyl/2-n-butyl 5-bismethylsulfonamido benzofuran and 8 g (0.2 mole) of sodium hydroxide in 190 ml of ethanol is stirred for 4 h. The mixture is then poured into a large volume of water and extracted 3 times with 50 ml of ethyl acetate. The organic solutions are pooled, washed with water, dried over sodium sulfate, filtered and evaporated to dryness in a vacuum. The residue is then purified by elution chromatography on a column of silica (eluant: ethyl acetate). The product obtained is then stirred in heptane until crystals are obtained.

In this manner, 4 g of 3-[4-(2-di-n-butylamino-ethoxy)benzoyl] 2-n-butyl 5-methylsulfonamido benzofuran are obtained after crystallization from heptane.

Yield: 74%
M.p.: 86° C.
Purity (HPLC): 98.08%

EXAMPLE 7

Preparation of 2-n-butyl
3-[4-(3-di-n-butylamino-propionamido)benzoyl]
5-amino benzofuran dioxalate (SR 34512A)

a) 4-(3-chloro propionamido) benzoic acid 13.7 g (0.1 mole) of p-aminobenzoic acid are dissolved in 100 ml ethyl acetate at 10° C. in a 250 ml round-bottomed flask. 9.5 ml (12.7 g; 0.1 mole) of 3-chloro propionyl chloride are then added with stirring at 10° C. After the mixture has been stirred for 1 h at 10° C., an aqueous solution of sodium acetate (25 g in 100 ml of water) is added and the reaction mixture is filtered. The colourless solid thus obtained is washed with water and dried.

In this manner, 13.2 g of 4-(3-chloro propionamido) benzoic acid are obtained in a yield of 58%.
M.p.: 225° C.

The following compound was prepared by following the same process as that described above: 4-(4-chloro butyramido)benzoic acid
Yield: 46%
M.p.: 220° C. (decomposition)

b) 4-(3-chloro propionamido)benzoyl chloride

A mixture of 13.2 g (0.058 mole) of 4-(3-chloro propionamido) benzoic acid in 100 ml of thionyl chloride are stirred and refluxed (70° C.) in a 250 ml round-bottomed flask equipped with a condenser and a calcium chloride guard tube. After 0.5 h, the thionyl chloride is evaporated and the crude reaction product is recrystallized from 200 ml of hot toluene. After evaporation, 11.91 g of 4-(3-chloro propionamido)benzoyl chloride are obtained.
Yield: 83%
M.p.: 130° C.

The following compound was prepared by following the same process as that described above: 4-(4-chloro butyramido)benzoyl chloride
Yield: 69%
M.p.: 100° C. (decomposition)

c) 3-[4-(3-chloro propionamido)benzoyl] 2-n-butyl 5-nitro benzofuran 11.91 g (0.048 mole) of 4-(3-chloro propionamido)benzoyl chloride and 10.61 g (0.048 mole) of 5-nitro 2-butyl benzofuran are dissolved in 280 ml of 1,2-dichloro ethane in a 500 ml round-bottomed flask fitted with a calcium chloride guard tube. 19.84 g (0.149 mole) of aluminium chloride are then added with vigorous stirring at 0° C. The reaction mixture is stirred at room temperature for 5 h, then poured onto 1 kg of crushed ice containing 50 ml of concentrated hydrochloric acid. After being stirred, the product formed is extracted twice with 250 ml of ethyl acetate. The organic phase are pooled, dried over sodium sulfate, filtered and the solvents are evaporated in a vacuum (1330 Pa). A crude solid is thus recovered weighing 19.7 g which is recrystallized from 250 ml of hot toluene.

In this manner, 10.9 g of 3-[4-(3-chloro propionamido)benzoyl] 2-n-butyl 5-nitro benzofuran are obtained.
Yield: 53%

The following compound was prepared by following the same process as that just described: 3-[4-(4-chloro butyramido)benzoyl] 2-n-butyl 5-nitro benzofuran
Yield: 77%
M.p.: about 100° C. (decomposition)

d) 2-n-butyl 3-[4-(3-di-n-butylamino propionamido)benzoyl] 5-nitro benzofuran oxalate 10.9 g (0.025 mole) of 3-[4-(3-chloro propionamido)benzoyl] 2-n-butyl 5-nitro benzofuran are dissolved in 50 ml of anhydrous benzene by refluxing in a 100 ml round-bottomed flask fitted with a condenser and a calcium chloride guard tube.

13 ml i.e. 9.9 g (0.076 mole) of di-n-butylamine are then added to the reaction mixture. After a reaction time of 5 h, the mixture is cooled and hydrolysed with 200 ml of water. It is extracted twice with 100 ml of ethyl acetate, then the organic phases are pooled and dried over sodium sulfate. After filtration, the solvents are evaporated in a vacuum (1330 Pa). The crude reaction product is chromatographed on 800 g of silica (eluant: dichloroethane/methanol 95/5) and 13.31 g of the desired compound (yield: 100%) are recovered in the form of the free base. The oxalic acid salt is formed in 250 ml of absolute ethanol and recovered by filtration.

In this manner, 2-n-butyl 3-[4-(3-di-n-butylamino propionamido)benzoyl] 5-nitro benzofuran oxalate is obtained.
M.p.: 147° C. (ethanol)

The following compound was prepared in the same manner as that just described: 2-n-butyl 3-[4-(4-di-n-butylamino-butyramido)benzoyl] 5-nitro benzofuran oxalate.
M.p.: 105° C.

e) 2-n-butyl
3-[4-(3-di-n-butylamino-propionamido)benzoyl]
5-amino benzofuran dioxalate 9.58 g (0.018 mole) of 2-n-butyl 3-[4-(3-di-n-butylaminopropionamido)benzoyl] 5-nitro benzofuran in the form of the free base are dissolved in 100 ml of absolute ethanol in a 250 ml round-bottomed flask. 0.958 g of 5% palladium on active charcoal are added and the reaction mixture is placed under an atmosphere of hydrogen. It is stirred vigorously for 5 h and filtered through a glass frit. The ethanolic solution thus recovered is treated with 3.24 g (0.036 mole) of oxalic acid so as to form the dioxalate which precipitates. It is filtered off and the salt is recrystallized from 100 ml of hot ethanol.

In this manner, 8.43 g of 2-n-butyl 3-[4-(3-di-n-butylamino-propionamido)benzoyl] 5-amino benzofuran dioxalate are obtained.
Yield: 70%
M.p.: 145° C.

EXAMPLE 8

Preparation of N-{2-n-butyl 3-[4-(3-di-n-butylamino propoxy)benzoyl] benzofuran-5-yl}1,3-propane sultam acid oxalate a) 5-amino 2-n-butyl benzofuran 8.8 g (0.04 mole) of 2-n-butyl 5-nitro benzofuran are stirred in 100 ml of ethanol in the presence of 0.6 g platinum oxide in a hydrogenation apparatus under a pressure of 3.4 atm. (50 p.s.i.) of hydrogen. When the pressure attains 2.7 atm. (40 p.s.i.), the reaction, which lasts about 20 min., is complete. The catalyst is filtered off and the filtrate is evaporated to dryness in a vacuum to give 7.3 g (yield: 96.56%) of a crude oily product.

In this manner, 5-amino 2-n-butyl benzofuran is obtained.

b) N-(2-n-butyl benzofuran-5-yl) 3-ammonium propane-1 sulfonate 2.85 g (0.015 mole) of 5-amino 2-n-butyl benzofuran and 1.85 g (0.015 mole) of 1,3-propane sultone are refluxed in 500 ml of acetonitrile for 1 h. The expected product precipitates during the reaction.

The mixture is allowed to cool, the product is filtered off, washed with ethyl ether and dried in a vacuum to give 2.9 g of product which is recrystallized from 450 ml of ethanol.

In this manner, 1.6 g of N-(2-n-butyl benzofuran-5-yl) 3-ammonium propane-1-sulfonate are obtained.
Yield: 34%
M.p.: 250°–253° C.

c) N-(2-n-butyl benzofuran-5-yl) 1,3-propane sultam

A mixture of 0.78 g (0.0025 mole) of N-(2-n-butyl benzofuran-5-yl)3-ammonium propane-1-sulfonate is triturated in a mortar with 1.05 g (0.005 mole) of phosphorous pentachloride. The mixture is then diluted with cold water, triturated, the product is filtered off, washed with water and dried in a vacuum. In this manner, 0.4 g of N-(2-n-butyl benzofuran-5-yl)1,3-propane sultam is obtained after recrystallization from cyclohexane.
Yield: 54.5%
M.p.: 84.5°–86° C.

d) N-[2-n-butyl 3-(4-methoxybenzoyl)benzofuran-5-yl] 1,3-propane sultam 16.25 g (0.0625 mole) of tin tetrachloride are added during 45 min. to a solution of 7.35 g (0.025 mole) of N-(2-n-butyl benzofuran-5-yl) 1,3-propane sultam and 5.55 g (0.0325 mole) of anisoyl chloride in 38 ml of dichloroethane. Stirring is continued for 3 h and the reaction mixture is poured onto a mixture of ice and water. Stirring is continued for a further 30 min., the organic phase is washed 3 times with 50 ml of water, once with 100 ml of a saturated solution of sodium hydrogen carbonate, then again with 100 ml of water. After evaporation, 9 g of product are obtained which are purified by elution chromatography on silica with chloroform as eluant. In this manner, 6 g of N-[2-n-butyl 3-(4-methoxybenzoyl)benzofuran-5-yl] 1,3-propane sultam are obtained after recrystallization from ethanol.
Yield: 56.1%
M.p.: 104°–107° C.

e) N-[2-n-butyl 3-(4-hydroxy benzoyl)benzofuran-5-yl] 1,3-propane sultam 2.15 g (0.005 mole) of N-[2-n-butyl 3-(4-methoxy benzoyl) benzofuran-5-yl] 1,3-propane sultam are refluxed for 4 h in 33 ml of dichloromethane in the presence of 2.66 g (0.02 mole) of aluminium chloride. The mixture is allowed to cool and poured onto a mixture of ice and water. The organic phase is extracted 3 times with 20 ml of 5% sodium hydroxide, then this solution is extracted twice with 25 ml of dichloromethane. The solution is acidified with concentrated hydrochloric acid and the acidic solution is stirred until crystallization occurred. Crystals are filtered off, washed with water and dried in a vacuum. In this manner, 1.8 g of N-[2-n-butyl 3-(4-hydroxy benzoyl)benzofuran-5-yl] 1,3-propane sultam are obtained.
Yield: 86.9%
M.p.: 79°–84° C.

f) N-{2-n-butyl 3-[4-(3-di-n-butylamino-propoxy)benzoyl]benzofuran-5-yl} 1,3-propane sultam acid oxalate This compound is obtained according to the method described in Example 1e.
M.p.: 75° C. (isopropanol)

EXAMPLE 9

2-n-butyl 3-{[4-(3-di-n-butylamino-propoxy)-phenyl]hydroxymethyl}5-methylsulfonamido benzofuran acid fumarate (SR 34173 A)

53.1 g (0.0954 mole) of 2-n-butyl 3-[4-(3-di-n-butylamino-propoxy)benzoyl] 5-methylsulfonamido benzofuran, 2.5 l of tetrahydrofuran and 285 ml of methanol are introduced into a 5 l round-bottomed flask cooled to 0° C. 5.7 g (0.152 mole) of sodium borohydride are then added in portions. After the addition is complete stirring is continued for a further 2 hours. The disappearance of the starting carbonyl compound is checked by thin layer chromatography (TLC) and 930 ml of water and 930 ml of dichloromethane are added to the reaction mixture. The organic phase is separated and the aqueous phase is extracted twice with 400 ml of dichloromethane. The organic phases are pooled, washed with water and dried over sodium sulfate. The solution is filtered and evaporated to dryness in a vacuum. Isopropyl ether is added to the residue obtained and heated. The insoluble material is discarded by hot filtration of the mixture and the expected product is allowed to crystallize in the form of the free base. It is taken up in ether and the fumarate is formed by the addition of fumaric acid in ether.

In this manner, 2-n-butyl 3-{[4-(3-di-n-butylaminopropoxy) phenyl]hydroxymethyl} 5-methylsulfonamido benzofuran acid fumarate is obtained.
Yield: 52.5%
M.p.: 94° C.

EXAMPLE 10

2-n-butyl 3-[4-(3-di-n-butylamino-propoxy)benzyl] 5-methylsulfonamido benzofuran (SR 34162)

100 ml of trifluoroacetic acid are introduced under a stream of nitrogen into a 500 ml round-bottomed flask cooled to 0° C. 0.6 g (0.016 mole) of sodium borohydride are then added in portions. Stirring is maintained for 0.5 h at 0° C. and a solution of 5.58 g (0.01 mole) of 2-n-butyl 3-{[4-(3-di-n-butylamino-propoxy)phenyl]hydroxymethyl}5-methylsulfonamido benzofuran in 500 ml of dichloromethane are added dropwise. When the addition is complete, stirring is continued for a further 40 min. at 0° C., then the excess sodium borohydride is destroyed by means of 5 ml of water. The mixture is evaporated to dryness in a vacuum and 250 ml of water and 250 ml of dichloromethane is added to the residue. The organic phase is separated. It is washed with a 2.5% solution of NaOH, then with water and dried over sodium sulfate. It is filtered and evaporated to dryness in a vacuum. The residue is purified by elution chromatography on silica with a dichloromethane/methanol 85/15 mixture. The crystalline product obtained is then stirred with hexane and filtered off.

In this manner, 2-n-butyl 3-[4-(3-di-n-butylamino-propoxy) benzyl] 5-methylsulfonamido benzofuran is obtained in a yield of 66.7%.

Purity (HPLC): 97.1%

EXAMPLE 11

Preparation of 5-amino 3-[4-(3-di-n-butylamino-propoxy)benzoyl]2-ethyl benzothiophene dioxalate (SR 34407 A)

a) 2-acetyl 5-nitro benzothiophene

A solution of 18.4 g (0.1 mole) of 2-chloro 5-nitro benzaldehyde in 80 ml of ethanol is heated to 50° C. A mixture of 12 g of sodium sulfide ($Na_2S$, 9 $H_2O$) and 1.6 g of sulfur are added with vigorous stirring. Heating is maintained at 50° C. for 0.5 h and a yellow precipitate is formed. The mixture is cooled to 20° C. and a solution of 6 g of sodium hydroxide and 6 g of sodium sulfide in 40 ml of water is added. Stirring at this temperature is maintained for a further 0.5 h to produce a red solution of 5-nitro 2-thio benzaldehyde. The mixture is cooled to 10° C. by means of an icebath and 9.2 g (0.1 mole) of chloroacetone are added. Stirring is maintained at room temperature for a further 2 h, then the mixture is poured into 200 ml of water. It is neutralized with acetic acid and the brown precipitate thus formed is filtered off. It is dried in a vacuum at a temperature of 50° C. to give 21 g of 2-acetyl 5-nitro benzothiophene which are purified by chromatography on a column of silica (eluant: dichloroethane/heptane 9/1).

M.p.: 103° C.
Yield: 85% b) 2-ethyl 5-nitro benzothiophene

A solution of 22.6 g (0.195 mole) of triethylamine in 50 ml of dichloromethane is cooled to 0° C. by means of an ice-sodium chloride bath. Boron trifluoride is then added to saturate the solution (about 25 g). A solution of 14.4 g (0.065 mole) of 2-acetyl 5-nitro benzothiophene in 50 ml of dichloromethane is added while the temperature is maintained at 0° C. Stirring is continued at 0° C. for 0.5 h while a very gentle stream of boron trifluoride is introduced. The complex formed is decomposed with a saturated solution of sodium chloride, the organic fraction is washed three times with a solution of sodium chloride and dried over anhydrous sodium sulfate. It is filtered and the solvent is evaporated at a rotary evaporator. In this manner, 16.6 g of 2-ethyl 5-nitro benzothiophene are obtained in the form of a yellow solid which is purified by chromatography on a column of silica (eluant: heptane/ethyl acetate 9/1).

M.p.: 55° C.
Yield: 61.9% c) 3-(4-methoxy benzoyl)2-ethyl 5-nitro benzothiophene 9 g (0.0434 mole) of 2-ethyl 5-nitro benzothiophene are dissolved in 300 ml of dichloroethane. The solution is cooled to 0° C. by means of an ice/sodium chloride bath. 28.9 g (0.217 mole) of aluminium chloride are then added in portions, followed by the dropwise addition of 7.5 g (0.0434 mole) of anisoyl chloride in 100 ml of dichloroethane. The mixture is stirred at room temperature for 3 h, poured onto ice and the organic fraction is washed twice with water. It is dried over anhydrous sodium sulfate, filtered and the solvent is evaporated at a rotary evaporator.

In this manner, 17 g of 3-(4-methoxy benzoyl) 2-ethyl 5-nitro benzothiophene are obtained which are purified by chromatography on a column of silica (eluant: heptane/ethyl acetate 7/3).

M.p.: 103° C.
Yield: 60.1% d) 3-(4-hydroxy benzoyl) 2-ethyl 5-nitro benzothiophene

A mixture of 7.7 g (0.0225 mole) of 3-(4-methoxy benzoyl) 2-ethyl 5-nitro benzothiophene and 35 g of pyridine hydrochloride are heated at 185° C. for 2.5 h. The mixture is cooled and taken up in 100 ml of water. The product is filtered off and washed on the filter with water and dried in a vacuum at a temperature of 50° C. After purification by chromatography on a column of silica (eluant: heptane/ethyl acetate 6/4), 5.6 g of 3-(4-hydroxy benzoyl) 2-ethyl 5-nitro benzothiophene are obtained.

M.p.: 210° C.
Yield: 76% e) 3-[4-(3-di-n-butylamino-propoxy)benzoyl] 2-ethyl 5-nitro benzothiophene acid oxalate This compound was obtained according to the method described in Example 1e.

M.p.: about 86° C. (diethyl ether)

The following compound was prepared in a similar manner: 3-{4-[3-(N-methyl N-3,4-dimethoxy-β-phenethyl)amino-propoxy]benzoyl} 2-ethyl 5-nitro benzothiophene hydrochloride.

M.p.: 168° C. (ethyl acetate/isopropanol 8/1)

f) 5-amino 3-[4-(3-di-n-butylamino-propoxy)benzoyl] 2-ethyl benzothiophene dioxalate This compound was obtained according to the method described in the Examples 1f and 2.

M.p.: 136° C. (ethyl acetate/ethanol 8/2)

EXAMPLE 12

Preparation of 5-amino 3-[4-(3-di-n-butylamino-propoxy)benzoyl] 2-n-butyl benzothiophene dihydrochloride (SR 34479 A) a) 2-butyroyl 5-nitro benzothiophene This compound was obtained in a manner similar to that described in Example 11a.

Yield: 52.2° C.
M.p.: 158° C.

b) 2-n-butyl 5-nitro benzothiophene

This compound was obtained according to a method similar to that described in Example 11b.

Viscous oil.
Yield: 72.3% c) 3-(4-hydroxy benzoyl) 2-n-butyl 5-nitro benzothiophene 7.8 g (0.033 mole) of 2-n-butyl 5-nitro benzothiophene are dissolved in 250 ml of dichloroethane. The solution is cooled to 0° C. by means of an ice/sodium chloride bath, then 22 g (0.165 mole) of aluminum chloride are added in portions. This is followed by the dropwise addition of 6 g (0.35 mole) of anisoyl chloride in 50 ml of dichloroethane. The mixture is stirred at room temperature for about 12 h, then poured onto ice. The organic fraction is washed twice with water, dried over anhydrous sodium sulfate, filtered and the solvent is evaporated at a rotary evaporator. The residual oil is then purified by chromatography on a column of silica (eluant: dichloroethane/ethyl acetate 98/2).

In this manner, 7.5 g of 3-(4-hydroxy benzoyl) 2-n-butyl 5-nitro benzothiophene are obtained.

Yield: 64.1%
M.p.: 147° C.

d) 3-[4-(3-di-n-butylamino-propoxy)benzoyl] 2-n-butyl 5-nitro benzothiophene acid oxalate This compound was obtained according to the method of Example 7e.

M.p.: ca. 88° C. (diethyl ether)

e) 5-amino 3-[4-(3-di-n-butylamino-propoxy)benzoyl] 2-n-butyl benzothiophene dihydrochloride This compound was obtained according to the method described in the Examples 1f and 2.

M.p.: 116° C. (diethyl ether)

EXAMPLE 13

Preparation of 5-amino 2-[4-(3-di-n-butylamino-propoxy)benzoyl] 3-n-butyl benzothiophene oxalate (SR 34224 A)

a) 3-n-butyl 5-nitro benzothiophene 2-carboxylic acid chloride 15.2 g (0.054 mole) of 3-n-butyl 5-nitro benzothiophene 2-carboxylic acid (RFA patent 2,854,014) are suspended in 50 ml of thionyl chloride and 1 ml of N,N-dimethylformamide. The suspension is stirred and heated until the dissolution of the acid is complete, then the excess thionyl chloride is distilled at a rotary evaporator. The solid residue is taken up in heptane, filtered off, the product is washed on the filter with heptane and dried in a vacuum at a temperature of 60° C.

In this manner, 16.4 g of 3-n-butyl 5-nitro benzothiophene 2-carboxylic acid chloride are obtained.

M.p.: 96° C.

b) 2-(4-hydroxy benzol) 3-n-butyl 5-nitro benzothiophene 7.3 g (0.0245 mole) of 3-n-butyl 5-nitro benzothiophene 2-carboxylic acid chloride are dissolved in 240 ml of dichloroethane, the solution is cooled to 0° C. and 26.3 g (0.122 mole) of aluminium chloride are added. After the mixture has been stirred for 0.5 h at 0° C., 7.94 g (0.0735 mole) of anisole are added. The mixture is allowed to attain room temperature, then is heated at 60° C. for 6 hours. It is poured into ice-cold water, the organic fraction is separated and the aqueous fraction is washed with dichloroethane. The organic fractions are pooled and washed with water, dried over sodium sulfate, filtered and the solvent is evaporated at a rotary evaporator. The residue is then purified by chromatography on a column of silica (eluant: dichloroethane/ethyl acetate 98/2).

In this manner, 2.7 g of 2-(4-hydroxy benzoyl)3-n-butyl 5-nitro benzothiophene are obtained.

Yield: 31%
M.p.: 182° C. (acetic acid/water 9/1).

c) 2-[4-(3-di-n-butylamino-propoxy)benzoyl]3-n-butyl 5-nitro benzothiophene 3.4 g (0.0095 mole) of 2-(4-hydroxy benzoyl)3-n-butyl 5-nitrobenzothiophene are dissolved in 100 ml of N,N-dimethylformamide. The solution is stirred, then 7 g of ground anhydrous potassium carbonate and 1.95 g (0.0095 mole) of di-n-butylaminopropyl chloride are added. The mixture is heated at 100° C. for 0.5 hour, cooled and the reaction product is poured into water. The mixture is extracted with ethyl acetate, the organic fraction is washed with water, dried over sodium sulfate, filtered and the ethyl acetate is evaporated at a rotary evaporator to give a thick oily residue. This is then purified by chromatography on a column of silica (eluant: dichloroethane/ethanol 9/1).

In this manner, 2-[4-(3-di-n-butylamino-propoxy)benzoyl]3-n-butyl 5-nitro benzothiophene is obtained.

d) 5-amino 2-[4-(3-di-n-butylamino-propoxy)benzoyl]3-n-butyl benzothiophene oxalate This compound was obtained according to the procedure described in the Examples 1f and 2.

M.P.: 135° C. (isopropanol)

EXAMPLE 14

Preparation of 3-[4-(3-di-n-butylamino-propoxy)benzoyl]2-n-butyl 5-nitro indole (SR 34127).

a) 2-n-butyl 5-nitro indole

A solution of 11 g (0.064 mole) of 2-n-butyl indole in 50 ml of concentrated sulfuric acid is cooled to 0° C. with the aid of an ice/sodium chloride cooling bath. While this temperature is maintained, a solution of 5.4 g of sodium nitrate in 50 ml of concentrated sulfuric acid is added dropwise (time of addition: 1.5 h). The mixture is stirred for a further 0.25 h and poured onto 400 g of crushed ice. The yellow precipitate is filtered off and washed with cold water on the filter.

In this manner, 13.5 g of 2-n-butyl 5-nitro indole are obtained.

Yield: 96.7%
M.p.: 105° C. (isopropanol/water 1/1)
Purity (HPLC): 99.1%

The following compound was prepared in a manner similar to that just described: 5-nitro 2-phenyl indole Yield: 95%
M.p.: 193° C. (isopropanol/water)

b) 3-(4-methoxy benzoyl) 2-n-butyl 5-nitro indole

A mixture of 20 g (0.091 mole) of 2-n-butyl 5-nitro indole and 16.2 g (0.091 mole) of 4-methoxy benzoyl chloride is stirred and heated at 150° C. for 0.25 h (end of hydrogen chloride evolution). The reaction mixture is taken up in dichloroethane, washed with water and the solvent is evaporated at a rotary evaporator (solid brown residue). The residue is then purified by chromatography on a column of silica (eluant: heptane/ethyl acetate 1/1).

In this manner, 23 g of 3-(4-methoxy benzoyl) 2-n-butyl 5-methoxy indole are obtained.

Yield: 72%
M.p.: 170° C. (heptane/isopropanol 8/2)
Purity (HPLC): 98.7%

The following compounds were prepared in a manner similar to that just described:

2-(4-methoxy benzoyl) 3-n-butyl 5-nitro indole
Yield: 62.9%
M.p.: 142° C. (heptane/ethyl acetate 7/3).

2-(4-methoxy benzoyl) 3-n-butyl 1-methyl 5-nitro indole
Yield: 64.5%
M.p.: 102° C. (ethanol)

c) 3-(4-hydroxy benzoyl) 2-n-butyl 5-nitro indole 12.3 g (0.035 mole) of 3-(4-methoxy benzoyl) 2-n-butyl 5-nitro indole and 40.4 g (0.35 mole) of pyridine hydrochloride are mixed and then heated at 180° C. for 1.5 hours. The mixture is taken up in water, acidified with hydrochloric acid and the brown precipitate is filtered off. It is washed with water on the filter and the crude product is then treated with a dilute solution of sodium hydroxide and 5 g of active charcoal. It is filtered through a fritted disc and the filtrate is acidified with hydrochloric acid. The precipitate is filtered off and washed with water on the filter. It is then dried in a vacuum at 60° C.

In this manner, 9.4 g of 3-(4-hydroxy benzoyl) 2-n-butyl 5-nitro indole are obtained.

Yield: 79.6%
M.p.: 230° C. (water/isopropanol 6/4)
Purity (HPLC): 99.6%

The following compounds were prepared in a manner similar to that just described:

2-(4-hydroxy benzoyl) 3-n-butyl 5-nitro indole
Yield: 77.7%
M.p.: 181° C. (water/isopropanol 8/2)

2-(4-hydroxy benzoyl) 3-n-butyl 1-methyl 5-nitro indole
Yield: 84.7%
M.p.: 172° C. (isopropanol/water 6/4)

3-(4-hydroxy benzoyl) 2-ethyl 1-methyl 4-nitro indole
M.p.: 191° C. (water/acetic acid 7/3)

d) 3-[4-(3-di-n-butylamino-propoxy)benzoyl] 2-n-butyl 5-nitro indole 5 g (0.015 mole) of 3-(4-hydroxy benzoyl) 2-n-butyl 5-nitro indole are dissolved in 100 ml of N,N-dimethylformamide, the solution is stirred and 12 g of ground anhydrous potassium carbonate and 3 g (0.015 mole) of di-n-butylaminopropyl chloride are added. The mixture is heated at 100° C. for 0.5 hour, cooled and the reaction product is poured into water. It is extracted with ethyl ether and the ethereal fraction is washed with water. It is dried over sodium sulfate, filtered and the ether is removed at a rotary evaporator which gives 5.1 g of an oily residue which is purified by chromatography on a column of silica (eluant: dichloroethane+5% ethanol).

In this manner, 2.9 g of 3-[4-(3-di-n-butylamino-propoxy)benzoyl] 2-n-butyl 5-nitro indole are obtained.
Yield: 38.1%
M.p.: 116° C.

EXAMPLE 15

Preparation of 5-amino 3-[4-(3-di-n-butylamino-propoxy)benzoyl] 2-n-butyl indole dioxalate (SR 34158 A).

4 g (0.0078 mole) of 3-[4-(3-di-n-butylamino-propoxy)benzoyl] 2n-butyl 5-nitro indole dissolved in 100 ml of ethanol and in the presence of 0.150 g of platinum oxide are hydrogenated at room temperature under a pressure of 7 kg/cm$^2$ (6.867×10$^5$ Pa). The mixture is filtered and the ethanol evaporated to give 3.5 g of a viscous oil (crude yield: 94.5%; purity (HPLC): 95%). The basic product thus obtained is then purified by chromatography on a column of silica (eluant: heptane/ethanol 9/1) and converted into the dioxalate in diethyl ether.

In this manner, 5-amino 3-[4-(3-di-n-butylamino-propoxy) benzoyl] 2-n-butyl indole dioxalate is obtained.

EXAMPLE 16

Preparation of 3-[4-(3-di-n-butylamino-propoxy)benzoyl] 2-n-butyl 5-methylsulfonamido indole hydrochloride (SR 34138 A)

A solution of 5 g (0.04 mole) of methanesulfonyl chloride in 20 ml of dichloroethane is added dropwise at room temperature and with stirring to a solution of 1.7 g (0.0035 mole) of 5-amino 3-[4-(3-di-n-butylamino-propoxy)benzoyl] 2-n-butyl indole and 0.6 g of triethylamine in 20 ml of dichloroethane. The mixture is stirred for 15 hours and the product of the reaction is washed twice with water. It is dried over sodium sulfate, filtered and the dichloroethane is evaporated to give 2.1 g of an oily residue which is purified by chromatography on a column of silica (eluant: heptane/ethyl acetate 1/1). 1 g of 3-[4-(3-di-n-butylamino-propoxy) benzoyl] 2-n-butyl 5-methylsulfonamido indole is thus recovered (yield: 52.6%; amorphous product) which is taken up in anhydrous ethyl ether. The hydrochloride is then formed by the addition of hydrogen chloride in ether.

In this manner, 0.9 g of 3-[4-(3-di-n-butylamino-propoxy) benzoyl] 2-n-butyl 5-methylsulfonamido indole hydrochloride is obtained.
M.p.: 112° C.
Purity (HPLC): 99.1%

EXAMPLE 17

Preparation of 3-[4-(3-di-n-butylamino-propoxy)benzoyl] 2-n-butyl 1-methyl 5-nitro indole hydrochloride (SR 34147 A)

a) 3-(4-methoxy benzoyl) 2-n-butyl 1-methyl 5-nitro indole 0.8 g (0.00303 mole) of 1,4,7,10,13,16-hexaoxacyclooctadecane and 3.9 g (0.0351 mole) of potassium tert.butoxide are added to 300 ml of benzene with stirring. After 0.25 hour, a solution of 10.7 g (0.0303mole) of 3-(4-methoxy benzoyl) 2-n-butyl 5-nitro indole in 60 ml of benzene is added. The mixture is stirred for 0.25 hour, then 5 g (0.0303 mole) of methyl iodide are added dropwise. The mixture is stirred for a further 18 hours at room temperature, then it is poured into water. The benzene fraction is separated, the aqueous fraction is washed with benzene, the benzene fractions are pooled and dried over sodium sulfate. The solution is filtered and the benzene is removed at a rotary evaporator to give a solid brown residue. This is then crystallized from an ethyl acetate/heptane 1/1 mixture.

In this manner, 10.3 g of 3-(4-methoxy benzoyl) 2-n-butyl 1-methyl 5-nitro indole are obtained.
M.p.: 168° C.
Purity (HPLC): 98%

The following compound was prepared in the same manner as that just described: 1-methyl 5-nitro 2-phenyl indole from 5-nitro 2-phenylindole
Yield: 92%
M.p.: 185° C. (isopropanol/heptane)

b) 3-(4-hydroxy benzoyl) 2-n-butyl 1-methyl 5-nitro indole 10.3 g (0.028 mole) of 3-(4-methoxy benzoyl) 2-n-butyl 1-methyl 5-nitro indole and 32.4 g (0.28 mole) of pyridine hydrochloride are mixed and then heated at 180° C. for 2 hours. The mixture is taken up in water, acidified with hydrochloric acid and the brown precipitate is filtered off. The crude product is washed on the filter with water, then treated with a dilute solution of sodium hydroxide and 4 g of active charcoal. It is filtered through a glass frit and the filtrate is acidified with hydrochloric acid. The precipitate formed is filtered off, washed on the filter with water and dried in a vacuum at 60° C.

In this manner, 9.3 g of 3-(4-hydroxy benzoyl) 2-n-butyl 1-methyl 5-nitro indole are obtained.
Yield: 88%
M.p.: 198° C. (isopropanol/water 6/4)
Purity (HPLC): 98.8% c) 3-[4-(3-di-n-butylamino-propoxy)benzoyl] 2-n-butyl 1-methyl 5-nitro indole hydrochloride This compound was prepared according to the procedure described in Example 14 paragraph d starting from 7 g (0.02 mole) of 3-(4-hydroxy benzoyl) 2-n-butyl 1-methyl 5-nitro indole, 150 ml of N,N-dimethylformamide, 15 g of ground anhydrous potassium carbonate and 4.1 g (0.02 mole) of di-n-butylaminopropyl chloride to give 9.1 g of the compound in the form of the free base (yield: 87.5%) The oily base crystallizes on being left to stand. It is purified by chromatography on a column of silica (eluant: heptane/ethanol 85/15)
M.p. (base): 84° C. (heptane)
M.p.: (hydrochloride): 140° C.

EXAMPLE 18

Preparation of 5-amino 3-[4-(3-di-n-butylamino-propoxy)benzoyl] 2-n-butyl 1-methyl indole dioxalate (SR 34156 A)

This compound was prepared according to the procedure of Example 15 starting from 6.5 g (0.0124 mole) of 3-[4-(3-di-n-butylamino-propoxy)benzoyl] 2-n-butyl 1-methyl 5-nitro indole, 150 ml of ethanol, 0.240 g of platinum oxide and hydrogen. The crude base obtained is in the form of a viscous oil (yield: 63.3%). It is purified by chromatography on a column of silica (eluant: heptane/ethanol 95/5) then converted into the dioxalate by treatment with a solution of oxalic acid in diethyl ether and recrystallized from ethanol.

In this manner, 5-amino 3-[4-(3-di-n-butylamino-propoxy) benzoyl] 2-n-butyl 1-methyl indole dioxalate is obtained.
M.p.: 168° C.
Purity (HPLC): 100%

EXAMPLE 19

Preparation of 3-[4-(3-di-n-butylamino-propoxy)benzoyl]2-n-butyl 5-methylsulfonamido 1-methyl indole hydrochloride (SR 34152 A)

This compound was obtained according to the procedure described in Example 16 starting from 3.4 g (0.007 mole) of 5-amino 3-[4-(3-di-n-butylamino-propoxy)-benzoyl] 2-n-butyl 1-methyl indole, 1.2 g of triethylamine, 40 ml of dichloroethane and 1.2 g (0.01 mole) of methanesulfonyl chloride in 40 ml of dichloroethane. The crude base obtained is purified by chromatography on a column of silica (eluant: heptane/ethanol 85/15). The base is obtained as an amorphous solid (yield: 50%; M.p.: ca. 80° C.).

The hydrochloride is then formed in ethyl ether by the addition of hydrogen chloride in ether.

In this manner, 1.6 g of 3-[4-(3-di-n-butylaminopropoxy) benzoyl] 2-n-butyl 5-methylsulfonamido 1-methyl indole hydrochloride are obtained.
M.p.: ca. 100° C.
Purity (HPLC): 98.14%

EXAMPLE 20

Preparation of 3-{4-[3-(N-methyl N-3,4-dimethoxy-β-phenethyl)aminopropoxy]benzoyl} 2-n-butyl 5-nitro indole (SR 35175 A)

a) 3-[4-(3-chloropropoxy)benzoyl] 2-n-butyl 5-nitro indole

A mixture of 2.18 g (0.01 mole) of 2-n-butyl 5-nitro indole and 2.33 g (0.01 mole) of 4-(3-chloropropoxy)-benzoyl chloride are stirred and heated at 150° C. for 0.25 h (end of evolution of hydrogen chloride). The reaction mixture is taken up in dichloroethane, washed with water and the solvent is removed at a rotary evaporator to give 4.9 g of crude product. It is then purified by chromatography on a column of silica (eluant: heptane/ethyl acetate 1/1).

In this manner, 2.8 g of 3-[4-(3-chloropropoxy)benzoyl] 2-n-butyl 5-nitro indole are obtained after recrystallization from a heptane/ethyl acetate 1/1 mixture.
Yield: 67.5%
M.p.: 125° C.
Purity (HPLC): 98.6% b) 3-{4-[3-(N-methyl N-3,4-dimethoxy-β-phenethyl)amino-propoxy]benzoyl} 2-n-butyl 5-nitro indole A mixture of 6.15 g (0.015 mole) of 3-[4-(3-chloropropoxy) benzoyl] 2-n-butyl 5-nitro indole, 4.8 g (0.02 mole) of N-methyl 3,4-dimethoxy β-phenethylamine hydrochloride, 9 g of anhydrous potassium carbonate, 1 g of 1,4,7,10,13,16-hexaoxacyclooctadecane and 75 ml of acetonitrile are stirred and heated at 60° C. for 6 h. The mixture is poured into water, extracted with ethyl ether and the ethereal fraction is washed twice with water. It is dried over sodium sulfate, filtered and the ether is removed at a rotary evaporator. The residue is then purified by chromatography on a column of silica (eluant: ethanol).

In this manner, 3.1 g of 3-{4-[3-(N-methyl N-3,4-dimethoxy-β-phenethyl)amino-propoxy]benzoyl} 2-n-butyl 5-nitro indole
Yield: 36.9%
M.p. (oxalate): 211° C.

EXAMPLE 21

Preparation of 5-amino 3-{4-[3-(N-methyl N-3,4-dimethoxy-β-phenethyl)amino-propoxy]benzoyl} 2-n-butyl indole dioxalate (SR 34176 A)

This compound was prepared according to the procedure described in Example 15 starting from 2.1 g (0.0054 mole) of 3-{4-/3-(N-methyl N-3,4-dimethoxy-β-phenethyl)amino-propoxy/benzoyl} 2-n-butyl 5-nitro indole, 75 ml of ethanol, 0.106 g of platinum oxide and hydrogen to give 2.8 g of a basic compound in the form of a gum (yield: 96.5%). The oxalate is then formed in a solution of tetrahydrofuran/ethyl ether 1/1).

In this manner, 5-amino 3-{4-[3-(N-methyl N-3,4-dimethoxy-β-phenethyl)amino-propoxy]benzoyl} 2-n-butyl indole dioxalate is obtained.
M.p.: 138° C. (ethanol)

EXAMPLE 22

Preparation of 3-{4-[3-(N-methyl N-3,4-dimethoxy-β-phenethyl)amino-propoxy]benzoyl} 2-n-butyl 5-methylsulfonamido indole hydrochloride (SR 34196 A)

This compound was prepared according to the procedure described in Example 16 starting from 2.1 g (0.00386 mole) of 5-amino 3-{4-[3-(N-methyl N-3,4-dimethoxy-β-phenethyl)amino-propoxy]benzoyl} 2-n-butyl indole, 0.6 g of triethylamine, 30 ml of dichloroethane and 0.48 g (0.0042 mole) of methanesulfonyl chloride in 20 ml of dichloroethane.

M.p.: 125° C. (isopropanol/ether)
Purity (HPLC): 99.8%

EXAMPLE 23

Preparation of 3-{4-[3-(N-methyl N-3,4-dimethoxy-β-phenethyl)amino-propoxy]benzoyl} 2-n-butyl 1-methyl 5-nitro indole oxalate (SR 34230 A)

a) 2-n-butyl 1-methyl 5-nitro indole 8.3 g (0.074 mole) of potassium tert.butoxide and 1.7 g of 1,4,7,10,13,16-hexaoxacyclooctadecane are stirred in 600 ml of benzene for 0.25 hour. A solution of 14 g (0.064 mole) of 2-n-butyl 5-nitro indole in 500 ml of benzene is then added. The mixture is stirred for 0.5 hour at room temperature and a solution of 9.1 g (0.064 mole) of methyl iodide in 100 ml of benzene is added. The mixture is stirred for a further 3 hours, washed with water and the benzene solution is dried over sodium sulfate. It is filtered and the solvent is evaporated at a rotary evaporator to give an oil which crystallizes on being left to stand.

In this manner, 13.6 g of 2-n-butyl 1-methyl 5-nitro indole are obtained.

Yield: 91.5%
M.p.: 77° C. (isopropanol/water 8/2)
Purity (HPLC): 99.6% b) 3-[4-(3-chloropropoxy)benzoyl] 2-n-butyl 1-methyl 5-nitro indole

This compound was prepared according to the procedure described in Example 20 paragraph a starting from 8.1 g (0.035 mole) of 2-n-butyl 1-methyl 5-nitro indole and 8.2 g (0.035 mole) of 4-(3-chloropropoxy)benzoyl chloride. The product obtained is purified by chromatography on a column of silica (eluant: dichloroethane/heptane 9/1).

In this manner, 3-[4-(3-chloropropoxy)benzoyl] 2-n-butyl 1-methyl 5-nitro indole is recovered in a yield of 60.1%.

M.p.: 125° C. (isopropanol)
Purity (HPLC): 98.1% c) 3-{4-[3-(N-methyl N-3,4-dimethoxy-β-phenethyl)amino-propoxy]benzoyl} 2-n-butyl 1-methyl 5-nitro indole oxalate This compound was obtained according to the procedure described in Example 20, paragraph b starting from 7.5 g (0.017 mole) of 3-[4-(3-chloropropoxy)benzoyl]2-n-butyl 1-methyl 5-nitro indole, 3.9 g (0.017 mole) of N-methyl 3,4-dimethoxy-β-phenethylamine hydrochloride, 10 g of anhydrous potassium carbonate, 1.1 g of 1,4,7,10,13,16-hexaoxacyclooctadecane and 100 ml of acetonitrile.

In this manner, 4.1 g of 3-{4-[3-(N-methyl N-3,4-dimethoxy-β-phenethyl) amino-propoxy]benzoyl} 2-n-butyl 1-methyl 5-nitro indole oxalate are obtained in the form of an oil.

Yield: 41%
M.p.: ca. 80° C. (isopropanol)

EXAMPLE 24

Preparation of 3-[4-(3-di-n-butylamino-propoxy)benzoyl] 2-n-butyl 1-di-n-butylaminopropyl 5-nitro indole (SR 34137A)

5 g (0.015 mole) of 3-(4-hydroxybenzoyl)2-n-butyl 5-nitro indole are dissolved in 100 ml of N,N-dimethylformamide. The solution is stirred, then 12 g of ground anhydrous potassium carbonate and 3 g (0.015 mole) of di-n-butylaminopropyl chloride are added. The reaction mixture is heated at 100° C. for 0.5 hour, then cooled and poured into water. It is extracted with ethyl ether and the ethereal fraction is washed with water. It is dried over sodium sulfate, filtered and the ether is removed at a rotary evaporator to give 5.1 g of an oily residue. This is then purified by chromatography on a column of silica (eluant: dichloroethane+5% ethanol).

In this manner, 1 g of 3-[4-(3-di-n-butylaminopropoxy) benzoyl] 2-n-butyl 1-di-n-butylaminopropyl 5-nitro indole is obtained.

M.p.: (dioxalate): 100° C. (isopropanol).

EXAMPLE 25

Preparation of 3-[4-(3-di-n-butylamino-propoxy)-benzoyl] 2-n-butyl 5-methylsulfonamido 1-methyl indole hydrochloride (SR 34152A)

2.45 g (0.005 mole) of 5-amino 3-[4-(3-di-n-butylamino-propoxy)benzoyl] 2-n-butyl 1-methyl indole and 1.34 g (0.0077 mole) of methanesulfonic acid anhydride are dissolved in 100 ml of dichloromethane. The solution is stirred, then 1 g of triethylamine is added. The mixture is stirred at room temperature for 24 hours and the solvent is evaporated at a rotary evaporator. The residue is taken up in ethyl acetate, washed with a 2N aqueous solution of sodium bicarbonate, then with water. It is dried over sodium sulfate, filtered and the ethyl acetate is removed at a rotary evaporator to give a residue which is purified by chromatography on a column of silica (eluant: dichloroethane+2.5% ethanol) and dried in a vacuum. The hydrochloride of the base thus obtained is then formed by the addition of hydrogen chloride in ether.

In this manner, 3-[4-(3-di-n-butylamino-propoxybenzoyl] 2-n-butyl 5-methyl sulfonamido 1-methyl indole hydrochloride is obtained.

M.p.: ca. 100° C.

EXAMPLE 26

Preparation of 3-[4-(3-di-n-butylamino-propoxy)benzoyl] 1-methyl 5-nitro 2-phenyl indole (SR 34432)

a) 3-(4-methoxy benzoyl) 1-methyl 5-nitro indole 10 g (0.039 mole) of silver trifluoromethanesulfonate are added to a solution of 6.66 g (0.039 mole) of anisoyl chloride in 100 ml of dichloromethane. The mixture is stirred for 1 h at room temperature and then 9.8 g (0.039 mole) of 1-methyl 2-phenyl indole are added. The mixture is then stirred at room temperature for a further 48 h, then 40 ml of a 2N solution of potassium hydroxide are added. The mixture is stirred vigorously for 12 h. It is filtered, the insoluble material is washed on the filter with a dichloroethane/isopropanol 1/1 mixture, then the organic fraction is washed twice with water. It is dried over anhydrous sodium sulfate, filtered and the solvent is removed at a rotary evaporator. The solid residue is dried under a vacuum at a temperature of 60° C. and recrystallized from a dichloroethane/isopropanol 1/1 mixture.

In this manner, 7 g of 3-(4-methoxy benzoyl) 1-methyl 5-nitro indole are obtained.
Yield: 47%
M.p.: 229° C.

b) 3-(4-hydroxy benzoyl) 1-methyl 5-nitro indole

This compound was obtained according to the method described in Example 14c.
Yield: 87.36%
M.p.: 260° C. (ethanol)

c) 3-[4-(3-di-n-butylamino-propoxy)benzoyl] 1-methyl 5-nitro 2-phenyl indole

This compound was obtained according to the method described in Example 14d
Yield: 80%
M.p.: 82° C.

EXAMPLE 27

Preparation of 3-[4-(3-di-n-butylamino-propoxy)benzoyl] 2-n-butyl 1-methylsulfonyl indole oxalate (SR 34353A)

0.227 g of sodium hydride (55% suspension in oil) is added to a solution of 2.2 g (0.00475 mole) of 3-[4-(3-di-n-butylaminopropoxy)benzoyl] 2-n-butyl indole in 50 ml of N,N-dimethylformamide and 25 ml of hexamethylphosphoramide. The reaction mixture is stirred at room temperature until the evolution of hydrogen ceased and then 0.544 g (0.00475 mole) of methanesulfonyl chloride in 10 ml of N,N-dimethylformamide are added. The reaction mixture is stirred for a further 15 h at room temperature, then it is poured into water. It is extracted with ethyl acetate, the organic fraction is washed twice with water and dried over anhydrous sodium sulfate. It is dried and the solvent is removed at a rotary evaporator to give 1.5 g of the desired compound in the form of the free base (viscous colourless oil; yield: 60%). The oxalate is then formed in an ethyl acetate/ethyl ether mixture.

In this manner, 3-[4-(3-di-n-butylamino-propoxy)-benzoyl] 2-n-butyl 1-methylsulfonyl indole oxalate is obtained.
M.p.: 90° C. (ethyl acetate/ethyl ether).

EXAMPLE 28

Preparation of 2-n-butyl 3-[4-(3-di-n-butylamino-propoxy)benzoyl] 7-carbethoxy indolizine acid oxalate (SR 34226A)

a) N-(hexanon-2-yl) 2-methyl 4-ethoxycarbonyl pyridinium bromide 19.5 g (0.118 mole) of 2-methyl 4-ethoxycarbonyl pyridine are dissolved in 35 g (0.196 mole) of 1-bromo hexan-2-one and left to stand at room temperature for about 15 hours. The solid mass is then triturated with anhydrous diethyl ether. It is filtered off, conveniently washed with the same solvent and dried in a vacuum.

In this manner, 37.5 g of N-(hexanon-2-yl) 2-methyl 4-ethoxycarbonyl pyridinium bromide are obtained.
Yield: 92%
M.p.: 139°-140° C.

The following compound is prepared in the same manner as that described above: N-phenylacetyl 2-methyl 4-ethoxycarbonyl pyridinium bromide
M.p.: 146°-147° C. (decomposition) (ethyl acetate/-methanol/diethyl ether)

b) 2-n-butyl 7-carbethoxy indolizine 33 g (0.101 mole) of N-(hexanon-2-yl) 2-methyl 4-ethoxycarbonyl pyridinium bromide are dissolved in 300 ml of absolute ethanol and the solution of 70 ml of triethylamine in 300 ml of absolute ethanol heated to reflux is added dropwise. After 2 h, the reaction mixture is evaporated to dryness and the residue is dissolved in ethyl acetate. The organic layer is washed with water, dried by means of magnesium sulfate and evaporated to dryness. The product obtained is then purified on a column of 800 g of silica (eluant: hexane/ethyl acetate).

In this manner, 17.4 g of 2-n-butyl 7-carbethoxy indolizine are obtained.
Yield: 70%
M.p.: 47°-48° C.

The following compound was prepared in the same manner as that described above: 2-phenyl 7-carbethoxy indolizine
M.p.: 143°-144° C. (methanol/dichlormethane)

c) 2-n-butyl 3-[4-(3-di-n-butylamino-propoxy)benzoyl] 7-carbethoxy indolizine acid oxalate A mixture of 0.35 g (38 mmoles) of 2-n-butyl 7-carbethoxy indolizine and 14.2 g (38 mmoles) of 4-(3-di-n-butylamino-propoxy) benzoyl chloride is heated at 95°-100° C. for 4.5 h. The crude product obtained is dissolved in ethyl acetate and water and is neutralized by sodium hydrogen carbonate. The organic layer is separated and dried over magnesium sulfate. It is filtered and the solvent evaporated. The residue is then purified on a column of silica with ethyl acetate as eluant in order to obtain 7.6 g of the desired compound in the form of the free base (yield: 97%). The oxalic acid salt is then formed in ethyl acetate and recovered by filtration.

In this manner, 2-n-butyl 3-[4-(3-di-n-butylaminopropoxy) benzoyl] 7-carbethoxy indolizine acid oxalate is obtained.
M.p.: 140°-142° C. (ethyl acetate/methanol)

EXAMPLE 29

Preparation of 2-n-butyl 3-[4-(3-di-n-butylamino-propoxy)benzoyl] 7-carboxy indolizine hydrochloride (SR 34227A)

7.60 g (14.02 mmoles) of 2-n-butyl 3-[4-(3-di-n-butylaminopropoxy)benzoyl] 7-carbethoxy indolizine are dissolved in 300 ml of ethanol containing 60 ml of a 1M a aqueous solution of sodium hydroxide. The mixture is refluxed for 24 h, then most of the ethanol is evaporated in a vacuum. 300 ml of water are added and the mixture is acidified by concentrated hydrochloric acid. The precipitate is extracted three times with 150 ml of dichloromethane, the extracts are pooled, dried and the solvents are evaporated.

In this manner, 6.13 g of 2-n-butyl 3-[4-(3-di-n-butylaminopropoxy)benzoyl] 7-carboxy indolizine hydrochloride are obtained:

Yield: 79%

M.p.: 190°-192° C. (ethyl acetate/methanol)

EXAMPLE 30

Preparation of 2-n-butyl 3-[4-(3-di-n-butylamino-propoxy)benzoyl] 7-benzyloxycarbamoyl indolizine (SR 34254)

7.10 g (13.08 mmoles) of 2-n-butyl 3-[4-(3-di-n-butylaminopropoxy)benzoyl] 7-carboxy indolizine are dissolved in 100 ml of anhydrous acetone containing 5.05 g (50 mmoles) of triethylamine. The mixture is cooled in an ice-cold waterbath and 1.70 g (15.67 mmoles) of ethyl chloroformate are added. After 1 h, a solution of 10 g (150 mmoles) of sodium azide in 70 ml of water are added. A yellow precipitate forms immediately. The mixture is left to stand for 45 min., then is poured into water. It is extracted with ethyl acetate, the organic layer is then dried over magnesium sulfate and the solvent is evaporated. The residue is dissolved in 30 ml of benzyl alcohol and the solution is heated at 105°-110° C. for 2 h. The solvent is removed by distillation in a vacuum and the crude carbamate is purified on a column of silica (eluant: ethyl acetate).

In this manner, 6.08 g of 2-n-butyl 3-[4-(3-di-n-butylaminopropoxy)benzoyl] 7-benzyloxycarbamoyl indolizine are obtained.

Yield: 75%

M.p.: 118°-119° C. (ethyl acetate)

EXAMPLE 31

Preparation of 2-n-butyl 3-[4-(3-di-n-butylamino-propoxy)benzoyl] 7-amino indolizine (SR 34399)

6.10 g (10 mmoles) of 2-n-butyl 3-[4-(3-di-n-butylaminopropoxy)benzoyl] 7-benzyloxycarbamoyl indolizine and 10% palladium on 0.550 g of active charcoal are stirred in 250 ml of absolute ethanol under an atmosphere of hydrogen for 60 h. The mixture is filtered through a glass frit and the filtrate is evaporated to give yellow crystals.

In this manner, 4.76 g of 2-n-butyl 3-[4-(3-di-n-butylaminopropoxy)benzoyl] 7-amino indolizine are obtained.

M.p.: 88°-89° C. (hexane)

EXAMPLE 32

Preparation of 2-n-butyl 3-[4-(3-di-n-butylamino-propoxy)benzoyl] 7-methylsulfonamido indolizine (SR 34255).

1.65 g (4.04 mmoles) of methanesulfonyl chloride in anhydrous dichloromethane are added to a solution of 2.85 g (5.975 mmoles) of 2-n-butyl 3-[4-(3-di-n-butylamino-propoxy)benzoyl] 7-amino indolizine in dichloromethane containing 10 ml of triethylamine (excess) with stirring at room temperature. The mixture is left to stand for 1 h, then is poured into water and extracted 3 times with 75 ml of dichloromethane. The fractions are pooled, dried over magnesium sulfate and the solvent is evaporated to give 3.47 g of the crude sulfonimide derivative. This sulfonimide is then dissolved in a solution of sodium hydroxide (2.0 g; 50 mmoles) in 250 ml of absolute ethanol at room temperature. After 45 min., the solution is dilited with 1 l of water and neutralized to pH=7 by concentrated hydrochloric acid which leads to the formation of a precipitate. The mixture is extracted 3 times with 150 ml of ethyl acetate, and the extracts are pooled, dried and evaporated. The residue is then purified on a column of silica with ethyl acetate as eluant.

In this manner, 2.59 g of 2-n-butyl 3-[4-(3-di-n-butylaminopropoxy)benzoyl] 7-methylsulfonamido indolizine are obtained.

Yield: 78%

M.p.: 87°-88° C. (hexane)

EXAMPLE 33

Preparation of 2-n-butyl 3-[4-(3-di-n-butylamino-propoxy)benzoyl] 7-carboxamido indolizine (SR 34296)

A mixture of 1 g (1.87 mmole) of 2-n-butyl 3-[4-(3-di-n-butylamino-propoxy)benzoyl] 7-carbethoxy indolizine, 5 ml of 25% ammonia and 25 ml of methanol are heated in a sealed tube for about 15 h at 100° C. The solution is evaporated to dryness and the residue dissolved in dichloromethane. The solution is washed with water, dried over magnesium sulfate and evaporated to dryness. The residue is purified on a column of silica with an ethyl acetate/methanol 9/1 mixture, then it is recrystallized from hexane/ethyl acetate.

In this manner, 0.485 g of 2-n-butyl 3-[4-(3-di-n-butylaminopropoxy)benzoyl] 7-carboxamido indolizine are obtained.

Yield: 51%

M.p.: 132° C. (hexane/ethyl acetate)

EXAMPLE 34

Preparation of 2-phenyl 3-[3-(3-di-n-butylamino-propoxy)benzoyl] 7-carbethoxy indolizine oxalate (SR 34507A)

a) 2-phenyl 3-(3-benzyloxy benzoyl) 7-carbethoxy indolizine

A mixture of 4 g (15.04 mmoles) of 2-phenyl 7-carbethoxy indolizine and 4 g (16.22 mmoles) of 3-benzyloxy benzoyl chloride is heated at 105°-110° C. for 4 h. The product obtained is purified on a column of silica with a hexane/ethyl acetate 4/1 mixture.

In this manner, 7.1 g of 2-phenyl 3-(3-benzyloxy benzoyl) 7-carbethoxy indolizine are obtained.

Yield: 90%

Oily product

The following compound is prepared in a manner similar to that described above: 2-phenyl 3-(4-benzyloxy benzoyl) 7-carbethoxy indolizine M.p.: 115°-117° C. (methanol/dichloromethane)

b) 2-phenyl 3-(3-hydroxy benzoyl) 7-carbethoxy indolizine 6.5 g (13.63 mmoles) of 2-phenyl 3-(3-benzyloxy benzoyl) 7-carbethoxy indolizine are dissolved in 300 ml of absolute ethanol containing 0.300 g of 5% palladized charcoal and 15 g of ammonium formate. The reaction mixture is refluxed for 24 h, then the catalyst is removed by filtration through a glass frit and the filtrate is evaporated to dryness. The residue is dissolved in ethyl acetate, the mixture is filtered and the salts are washed 3 times with ethyl acetate. The solvent is evaporated and the crude product is purified on a column of silica (eluant: hexane/ethyl acetate 1/1).

In this manner, 4.16 g of 2-phenyl 3-(3-hydroxy benzoyl) 7-carbethoxy indolizine are obtained.

Yield: 83%

M.p.: 193°-195° C. (hexane/ethyl acetate).

The following compound was prepared in a manner similar to that described above. 2-phenyl 3-(4-hydroxy benzoyl) 7-carbethoxy indolizine M.p.: 135° C. (ethyl acetate/hexane)

c) 2-phenyl 3-[3-(3-di-n-butylamino-propoxy)benzoyl] 7-carbethoxy indolizine 0.387 g (1 mmole) of 2-phenyl 3-(3-hydroxy benzoyl) 7-carbethoxy indolizine and 0.206 g (1 mmole) of 3-di-n-butylamino 1-chloro propane are dissolved in 3 ml of anhydrous dimethylsulfoxide containing 0.3 g of potassium carbonate and a catalytic amount of sodium iodide. The reaction mixture is maintained at room temperature under nitrogen for 5 days, then is poured into water and extracted with ethyl acetate. The extracts are dried over magnesium sulfate and evaporated. The residue is then purified on a column of silica (eluant: ethyl acetate).

In this manner, 0.503 g of 2-phenyl 3-[3(3-di-n-butylamino-propoxy)benzoyl] 7-carbethoxy indolizine is obtained.

Yield: 91%

The oxalate of this compound is found to be amorphous.

EXAMPLE 35

Preparation of 3-{2-[5-(3-di-n-butylamino-propoxy)thenoyl]} 5-bismethylsulfonamido 2-n-butyl benzofuran a) 5-(bismethylsulfonamido) 2-n-butyl benzofuran A solution of 26.45 g (0.231 mole) of methanesulfonyl chloride in 175 ml of carbon tetrachloride is added dropwise during 1.5 h to a solution of 14.6 g (0.077 mole) of 5-amino 2-n-butyl benzofuran in 500 ml of carbon tetrachloride containing 77.9 g (0.77 mole) of triethylamine. The temperature rises to 30° C. The reaction mixture is then refluxed for 6 h. It is allowed to cool, poured into a mixture of ice and water, the organic phase is separated and the aqueous phase is extracted 3 times with 150 ml of methylene chloride. The combined organic phases are washed 3 times with 250 ml of water, dried, filtered and evaporated to dryness in a vacuum.

In this manner, 20.1 g of 5-(bismethylsulfonamido) 2-n-butyl benzofuran after recrystallization from isopropanol are obtained.

Yield: 75.5%
M.p.: 126° C.
Purity (HPLC): 99.5% b) 3-[5-bismethylsulfonamido 2-(5-methoxy thenoyl)]2-n-butyl benzofuran

A solution of 7.3 g (0.028 mole) of tin tetrachloride in 10 ml of chloroform is added during 10 min. and at a temperature of 24° C. to a solution of 6.9 g (0.02 moles) of 5-bismethylsulfonamido 2-n-butyl benzofuran in 40 ml of chloroform. A solution of 1.77 g (0.01 mole) of 5-methoxy thenoyl chloride in 15 ml of chloroform is then added during 3.5 h. The reaction mixture is stirred for 48 h and then poured into 60 ml of 2N hydrochloric acid. The phases are separated and the aqueous phase is extracted twice with 50 ml of ethyl ether. The combined organic phases are washed with 40 ml of water, 40 ml of 2N sodium hydroxide, 35 ml of water, then dried over sodium sulfate. They are filtered and evaporated to dryness in a vacuum. The residue is purified by chromatography on silica with chloroform as eluant.

In this manner, 4.2 g of 3-[5-bismethylsulfonamido 2-(5-methoxy thenoyl)] 2-n-butyl benzofuran are obtained after recrystallization from ethanol.

Yield: 43.2%
M.p.: 164°-166° C.
Purity (HPLC): 99.5% c) 3-[5-bismethylsulfonamido 2-(5-hydroxy thenoyl)]2-n-butyl benzofuran

A solution of 17 ml (0.017 mole) of boron tribromide (1M solution in methylene chloride) is added during 10 min. to a solution of 2.45 g (0.005 mole) of 3-[5-bismethylsulfonamido 2-(5-methoxy thenoyl)] 2-n-butyl benzofuran in 20 ml of chloroform at a temperature from 15° to 20° C.

The reaction mixture is refluxed for 4 h, then poured into a mixture of ice and water to which 50 ml of 2N hydrochloric acid is subsequently added. The solid formed is filtered off and the aqueous phase is extracted twice with 40 ml of methylene chloride. The combined extracts are washed with water, dried over sodium sulfate, filtered and evaporated to dryness.

In this manner, 2 g of 3-[5-bismethylsulfonamido 2-(5-hydroxy thenoyl)] 2-n-butyl benzofuran are obtained as a solid.

Yield: 84.8%
M.p.: 202°-204° C.
Purity (HPLC): 99.6% d) 3-{2-[5-(3-di-n-butylamino-propoxy)thenoyl]} 5-bismethylsulfonamido 2-n-butyl benzofuran This compound was obtained according to the method described in Example 1e.

The following compounds have been prepared using the methods previously described in the examples:

5-amino 3-[4-(3-di-n-butylamino-propoxy)benzoyl] 2-isopropyl benzofuran (Ex. 36)
Oil
Purity (HPLC): 97.84%

5-amino 3-[4-(3-di-n-butylamino-propoxy)benzoyl] 2-phenyl benzofuran hemioxalate (Ex. 37)
M.p.: 104° C. (methanol)
Purity (HPLC): 98.2%

5-amino 2-n-butyl 3-[4-(3-n-butylamino-propoxy)benzoyl] benzofuran (Ex. 38)
Oil
Purity (HPLC): 97.83%

5-amino 3-[4-(3-di-n-butylamino-propoxy)3,5-dimethylbenzoyl] 2-n-butyl benzofuran hydrochloride (SR 33750 A) (Ex. 39)
M.p.: 160°-161° C. (ethyl acetate)

5-amino 3-[4-(3-tert.butylamino-propoxy)benzoyl]2-n-butyl benzofuran dioxalate (SR 33667 A) (Ex. 40)
M.p.: 146° C. (methanol)

5-amino 3-{4-[3-(N-methyl N-3,4-dimethoxy-β-phenethyl)amino-propoxy]benzoyl} 2-n-butyl benzofuran dioxalate (SR 33665 A) (Ex. 41)
M.p.: 163° C. (methanol)

5-n-butylsulfonamido 3-[4-(3-di-n-butylamino-propoxy)benzoyl]2-n-butyl benzofuran (SR 34193) (Ex. 42)
M.p.: 78° C.

3-[4-(3-di-n-butylamino-propoxy)benzoyl]2-n-butyl 5-tolysulfonamido benzofuran acid fumarate (SR 34088 A) (Ex. 43)
M.p.: 110° C. (isopropanol)

2-n-butyl 3-[4-(3-n-butylamino-propoxy)benzoyl]5-methylsulfonamido benzofuran (SR 34174) (Ex. 44)
M.p.: 86° C.

2-n-butyl 3-[4-(3-di-n-butylamino-propoxy)benzoyl] 5-methylsulfonamido benzofuran oxalate (SR 33589 A) (Ex. 45)
M.p.: 75° C. (acetone/hexane)

2-n-butyl 3-[4-(3-di-n-butylamino-propoxy)benzoyl] 5-trifluoromethylsulfonamido benzofuran hydrochloride (SR 34099 A) (Ex. 46)
M.p.: 60° C. (petroleum ether 40°-60° C.)

2-n-butyl 3-{4-[3-(N-methyl N-3,4-dimethoxy-β-phenethyl)amino-propoxy] benzoyl} 5-methylsulfonamido benzofuran hydrochloride (SR 33666 A) (Ex. 47)
M.p.: 120° C. (dichloromethane/ether)

2-n-butyl 3-[4-(3-di-n-butylamino-propoxy)3,5-dimethyl benzoyl] 5-methylsulfonamido benzofuran hemioxalate (SR 33751 A) (Ex. 48)
M.p.: 71° C.

2-phenyl 3-[4-(3-di-n-butylamino-propoxy)benzoyl] 5-methylsulfonamido benzofuran (SR 34150) (Ex. 49)
M.p.: 40° C.

2-isopropyl 3-[4-(3-di-n-butylamino-propoxy)benzoyl]5-methylsulfonamido benzofuran p-toluenesulfonate (SR 34153 A) (Ex. 50)
M.p.: 128° C. (isopropanol)

2-isopropyl 3-[4-(3-di-n-butylamino-propoxy)benzoyl] 5-N,N-bis (methylsulfonyl)amino benzofuran p-toluenesulfonate (Ex. 51)
M.p.: 142° C. (isopropanol)

5-amino 3-[4-(3-di-n-butylamino-propoxy)benzoyl]2-methyl benzofuran dioxalate (SR 34287 A) (Ex. 52)
M.p.: 136° C. (methanol)
Purity (HPLC): 99.3%

5-amino 3-[4-(3-di-n-butylamino-propoxy)benzoyl] 2-isopropyl benzofuran (Ex. 53)
Oil
Purity (HPLC): 97.84%

5-amino 3-[4-(3-di-n-butylamino-propoxy)benzoyl] 2-phenyl benzofuran (Ex. 54)
Oil
Purity (HPLC): 98.2%

5-amino 3-[4-(3-di-n-butylamino-propoxy)benzoyl] 2-n-propyl benzofuran (Ex. 55)

5-amino 3-[4-(3-di-n-butylamino-propoxy)benzoyl] 2-ethyl benzofuran dioxalate (SR 34521 A) (Ex. 56)
M.p.: 172° C. (methanol)
Purity (HPLC): 99.25%

5-amino 2-n-butyl 3-[4-(3-diethylamino-propoxy)benzoyl]benzofuran dihydrochloride (SR 34520 A) (Ex. 57)
M.p.: 121.5° C. (ethanol)
Purity (HPLC): 98.7%

7-amino 3-[4-(3-di-n-butylamino-propoxy)benzoyl]2-methyl benzofuran dihydrochloride (SR 34405 A) (Ex. 58)
M.p.: 160° C.
Purity (HPLC): 97.5%

5-amino 2-[4-(3-di-n-butylamino-propoxy)benzoyl]3-methyl benzofuran dihydrochloride (SR 34433 A) (Ex. 59)
M.p.: 178° C. (isopropanol)
Purity (HPLC): 99.2%

5-amino 2-n-butyl 3-[4-(5-di-n-butylamino-pentoxy)benzoyl] benzofuran dioxalate (SR 34486 A) (Ex. 60)
M.p.: 95° C. (isopropanol)
Purity (HPLC): 98.91%

5-amino 2-n-butyl 3-[4-(3-n-butylamino-propoxy)benzoyl]benzofuran (Ex. 61)
Oil
Purity (HPLC): 97.83%

3-[4-(3-di-n-butylamino-propoxy)benzoyl] 5-methylsulfonamido 2-phenyl benzofuran (SR 34150) (Ex. 62)
M.p.: 40° C.
Purity (HPLC): 98.29%

3-[4-(3-di-n-butylamino-propoxy)benzoyl] 2-methyl 5-methylsulfonamido benzofuran hydrochloride (SR 34144 A) (Ex. 63)
M.p.: 163° C. (ethanol)
Purity (HPLC): 99.75%

3-[4-(3-di-n-butylamino-propoxy)benzoyl] 2-isopropyl 5-methylsulfonamido benzofuran p-toluenesulfonate (SR 34153 A) (Ex. 64)
M.p.: 128° C. (isopropanol)
Purity (HPLC): 98%

3-[4-(3-di-n-butylamino-propoxy)benzoyl]2-n-butyl 5-n-butylsulfonamido benzofuran (SR 34193) (Ex. 65)
M.p.: 78° C.
Purity (HPLC): 99.82%

2-n-butyl 3-[4-(3-di-n-butylamino-propoxy)benzoyl] 5-trifluoromethylsulfonamido benzofuran hydrochloride (SR 34099 A) (Ex. 66)
M.p.: 50°-55° C.
Purity (HPLC): 99.4%

2-n-butyl 3-[4-(3-di-n-butylamino-propoxy)benzoyl] 5-tosylamino benzofuran acid fumarate (SR 34088 A) (Ex. 67)
M.p.: 110° C. (isopropanol)
Purity (HPLC): 98.24%

2-n-butyl 3-[4-(3-n-butylamino-propoxy)benzoyl]5-methylsulfonamido benzofuran (SR 34174) (Ex. 68)
M.p.: 86.4° C.
Purity (HPLC): 99.57%

3-[4-(3-di-n-butylamino-propoxy)benzoyl] 2-methyl 7-methylsulfonamido benzofuran acid oxalate (SR 34436 A) (Ex. 69)
M.p.: 135° C. (methyl ethyl ketone)
Purity (HPLC): 99.1%

3-[4-(3-di-n-butylamino-propoxy)benzoyl]5-bismethylsulfonamido 2-n-butyl benzofuran (SR 34477) (Ex. 70)
M.p.: 56° C. (hexane)
Purity (HPLC): 99.7%

3-[4-(3-di-n-butylamino-propoxy)benzoyl]5-bismethylsulfonamido 2-n-propyl benzofuran (SR 34555 A) (Ex. 71)
M.p.: 57° C. (pentane)
Purity (HPLC): 99.8%

3-[4-(3-diethylamino-propoxy)benzoyl] 2-n-butyl 5-bismethylsulfonamido benzofuran (SR 34505) (Ex. 72)
M.p.: 83° C.
Purity (HPLC): 98.9%

3-[4-(2-di-n-butylamino-ethoxy)benzoyl]5-bismethylsulfonamido 2-n-butyl benzofuran p-toluenesulfonate (Ex. 73)
M.p.: 142° C. (ethyl acetate)
Purity (HPLC): 98.42%

3-[4-(5-di-n-butylamino-pentoxy)benzoyl]5-bismethylsulfonamido 2-n-butyl benzofuran (SR 34343) (Ex. 74)
M.p.: 84° C.
Purity (HPLC): 97.1%

3-[4-(3-di-n-butylamino-propoxy)benzoyl]7-bismethylsulfonamido 2-methyl benzofuran (SR 34403) (Ex. 75)
M.p.: 108° C.
Purity (HPLC): 96.7%

2-[4-(3-di-n-butylamino-propoxy)benzoyl] 5-bismethylsulfonamido 3-methyl benzofuran (SR 33602) (Ex. 76)
M.p.: 125° C. (methanol)
Purity (HPLC): 99%

3-[4-(3-di-n-butylamino-propoxy)benzoyl]5-bismethylsulfonamido 2-isopropyl benzofuran p-toluenesulfonate (SR 34154 A) (Ex. 77)
M.p.: 142° C. (isopropanol)
Purity (HPLC): 98%

3-[4-(5-di-n-butylamino-pentoxy)benzoyl] 2-n-butyl 5-methylsulfonamido benzofuran (SR 34492) (Ex. 78)
M.p.: 55° C.
Purity (HPLC): 96.21%

3-[4-(3-di-n-butylamino-propoxy)benzoyl] 2-ethyl 5-methylsulfonamido benzofuran dioxalate (SR 34536 A) (Ex. 79)
M.p.: 111° C. (ethyl acetate)

3-[4-(3-di-n-butylamino-propoxy)benzoyl] 2-n-propyl 5-methylsulfonamido benzofuran acid oxalate (Ex. 80) M.p.: 145°-147° C.

3-[4-(3-diethylamino-propoxy)benzoyl] 2-n-butyl 5-methylsulfonamido benzofuraN (SR 34523 A) (Ex. 81)
M.p.: 65° C.
Purity (HPLC): 96.33%

2-[4-(3-di-n-butylamino-propoxy)benzoyl] 3-methyl 5-methylsulfonamido benzofuran hydrochloride (SR 34474 A) (Ex. 82)
M.p.: 90° C.
Purity (HPLC): 99.6%

3-[4-(3-di-n-butylamino-propoxy)benzoyl] 2-isopropyl 5-methylsulfonamido benzofuran p-toluenesulfonate (Ex. 83)
M.p.: 128° C. (isopropanol)
Purity (HPLC): 99%

5-amino 3-{4-[3-(N-methyl N-3,4-dimethoxy-β-phenethyl)amino-propoxy] benzoyl} 2-ethyl benzothiophene dihydrochloride (SR 34453 A) (Ex. 84)
Yield: 81.2%
M.p.: 138° C. (diethyl ether)

3-[4-(3-di-n-butylamino-propoxy)benzoyl]2-ethyl 5-methylsulfonamido benzothiophene hydrochloride (SR 34413 A) (Ex. 85)
M.p.: 94° C.

3-{4-[3-(N-methyl N-3,4-dimethoxy-β-phenethyl)amino-propoxy]benzoyl} 2-ethyl 5-methylsulfonamido benzothiophene hydrochloride (SR 34463 A) (Ex. 86)
M.p.: ca. 110° C. (diethyl ether/tetrahydrofuran)

3-[4-(3-di-n-butylamino-propoxy)benzoyl]2-n-butyl 5-methylsulfonamido benzothiophene hydrochloride (SR 34489 A) (Ex. 87)
M.p.: ca. 82° C. (diethyl ether)

5-amino 2-{4-[3-(N-methyl-N-3,4-dimethoxy-β-phenethyl)amino-propoxy] benzoyl}3-n-butyl benzothiophene sesquioxalate (SR 34340 A) (Ex. 88)
M.p.: ca. 120° C. (ethyl acetate/ethanol 7/3)

2-[4-(3-di-n-butylamino-propoxy)benzoyl]3-n-butyl 5-methylsulfonamido benzothiophene hydrochloride (SR 34232 A) (Ex. 89)
M.p.: ca. 90° C. (diethyl ether)

2-{4-[3-(N-methyl N-3,4-dimethoxy-β-phenethyl)amino-propoxy]benzoyl} 3-n-butyl 5-methylsulfonamido benzothiophene oxalate (SR 34371 A) (Ex. 90)
M.p.: 136° C. (ethyl acetate/isopropanol 9/1)

5-amino 3-{4-[3-(N-methyl N-3,4-dimethoxy-β-phenethyl)amino-propoxy] benzoyl} 2-n-butyl 1-methyl indole oxalate (SR34225 A) (Ex. 91)
M.p.: 188° C. (ethanol)

3-{4-[3-(N-methyl N-3,4-dimethoxy-β-phenethyl)amino-propoxy] benzoyl} 2-n-butyl 1-methyl 5-methylsulfonamido indole fumarate (SR 34291 A) (Ex. 92)
M.p.: 166° C. (ethyl acetate)

5-amino 3-[4-(3-di-n-butylamino-propoxy)benzoyl]2-n-butyl 1-di-n-butylaminopropyl indole methanesulfonate (SR 34294 A) (Ex. 93)
Hygroscopic
M.p.: ca. 85° C. (ethyl ether)

2-[4-(3-di-n-butylamino-propoxy)benzoyl] 3-n-butyl 5-nitro indole (SR 34358) (Ex. 94)
M.p.: 80° C. (heptane)

2-[4-(3-di-n-butylamino-propoxy)benzoyl]3-n-butyl 1-di-n-butylaminopropyl 5-nitro indole dioxalate (SR 34359 A) (Ex. 95)
M.p.: 79° C. (isopropanol/diethyl ether)

2-[4-(3-di-n-butylamino-propoxy)benzoyl]3-n-butyl 1-methyl 5-nitro indole methanesulfonate (SR 34305 A) (Ex. 96)
M.p.: 115° C. (ethyl acetate)

3-[4-(3-di-n-butylamino-propoxy)benzoyl]2-ethyl 1-methyl 4-nitro indole oxalate (SR 34532 A) (Ex. 97)
M.p.: ca. 84° C.

3-{4-[3-(N-methyl N-3,4-dimethoxy-β-phenethyl)amino-propoxy]benzoyl} 2-n-butyl 1-methyl 5-nitro indole oxalate (SR 34230 A) (Ex. 98)
M.p.: ca. 80° C. (isopropanol)

3-[4-(3-di-n-butylamino-propoxy)benzoyl]2-n-butyl 1-di-n-butylaminopropyl 5-methanesulfonamido indole (SR 34304 A) (Ex. 99)
M.p.: 81° C. (hexane)

3-[4-(3-di-n-butylamino-propoxy)benzoyl]2-n-butyl 1-di-n-butylaminopropyl 5-trifluoromethylsulfonamido indole (SR 34334) (Ex. 100)
M.p.: 142° C. (heptane/ethyl acetate)

3-[4-(3-di-n-butylamino-propoxy)benzoyl]1-methyl 2-phenyl 5-methylsulfonamido indole (SR 34451) (Ex. 101)
M.p.: 116° C. (diethyl ether)

5-amino 3-{4-[3-(N-methyl N-3,4-dimethoxy-β-phenethyl)amino-propoxy] benzoyl} 2-n-butyl 1-methyl indole oxalate (SR 34225 A) (Ex. 102)
M.p.: 188° C. (ethanol)

5-amino 3-[4-(3-di-n-butylamino-propoxy)benzoyl]1-methyl 2-phenyl indole dihydrochloride (SR 34443 A) (Ex. 103)
M.p.: 154° C. (diethyl ether)

5-amino 2-[4-(3-di-n-butylamino-propoxy)benzoyl]3-n-butyl 1-methyl indole oxalate (SR 34333 A) (Ex. 104)
M.p.: 110° C. (isopropanol)

5-amino 2-4-(3-di-n-butylamino-propoxy)benzoyl]3-n-butyl 1-di-n-butylaminopropyl indole trihydrochloride (SR 34449 A) (Ex. 105)
M.p.: 130° C. (diethyl ether)

2-[4-(3-di-n-butylamino-propoxy)benzoyl]3-n-butyl 1-methyl 5-methylsulfonamido indole fumarate (SR 34227 A) (Ex. 106)
M.p.: ca. 85° C. (ethanol/diethyl ether)

3-[4-(3-di-n-butylamino-propoxy)benzoyl]2-n-butyl 1-(4-methyl benzenesulfonyl) indole oxalate (SR 34376 A) (Ex. 107)
M.p.: 98° C. (ethyl ether)

4-amino 3-[4-(3-di-n-butylamino-propoxy)benzoyl]2-ethyl 1-methyl indole oxalate (Ex. 108)
M.p.: 86° C. (diethyl ether)

3-[4-(3-di-n-butylamino-propoxy)benzoyl]2-ethyl 1-methyl 4-methylsulfonamido indole (Ex. 109) (SR 34563 A)
M.p.: 150° C. (ethyl acetate/isopropanol)

2-phenyl 3-[4-(3-di-n-butylamino-propoxy)benzoyl]7-carbethoxy indolizine acid oxalate (SR 34400 A) (Ex. 110)
M.p.: 148°-151° C. (ethyl acetate/methanol)

2-phenyl 3-[4-(3-di-n-butylamino-propoxy)benzoyl]7-carboxy indolizine hydrochloride (SR 34401 A) (Ex. 111)
M.p.: 222°-224° C. (ethyl acetate/methanol 2-phenyl 3-[4-(3-di-n-butylamino-propoxy)benzoyl]7-benzyloxycarbamoyl indolizine oxalate (SR 34402 A) (Ex. 112)
M.p.: 177°-178° C. (ethyl acetate/methanol/diethyl ether)

2-phenyl 3-[4-(3-di-n-butylamino-propoxy)benzoyl]7-amino indolizine (SR 34408) (Ex. 113)
M.p: 102°-103° C. (hexane)

2-phenyl 3-[4-(3-di-n-butylamino-propoxy)benzoyl]7-methylsulfonamido indolizine hydrochloride (SR 34417 A) (Ex. 114)
M.p.: 190°-191° C. (ethyl acetate/methanol)

2-n-butyl 3-[4-(3-di-n-butylamino-propxy)benzoyl]7-N-methylcarboxamido indolizine (SR 34330) (Ex. 115)
M.p: 94° C. (hexane/dichloromethane)

2-n-butyl 3-[4-(3-di-n-butylamino-propoxy)benzoyl]7-pyrrolidinocarbonyl indolizine acid oxalate (SR 34329 A) (Ex. 116)
M.p.: 143°-144° C. (ethyl acetate/dichloromethane)

2-phenyl 3-{4-[3-(N-methyl N-3,4-dimethoxy-β-phenethyl)amino-propoxy] benzoyl}7-carbethoxy indolizine oxalate (SR 34484 A) (Ex. 117)
M.p.: 162° C. (methanol)

2-phenyl 3-[3-(3-di-n-butylamino-propoxy)benzoyl]7-carboxy indolizine hydrochloride (Ex. 118)
M.p.: 210°-215° C. (ethyl acetate/methanol)

2-phenyl 3-{4-[3-(N-methyl N-3,4-dimethoxy-β-phenethyl)amino-propoxy] benzoyl}7-carboxy indolizine hydrochloride (SR 34506 A) (Ex. 119)
M.p.: 128°-130° C. (ethyl acetate/methanol)

2-n-butyl 3-[4-(3-di-n-butylamino-propionamido)benzoyl]5-methylsulfonamido benzofuran oxalate (SR 34335 A) (Ex. 120)
M.p.: 162° C. (methanol/diethyl ether)

2-n-butyl 3-[4-(3-di-n-butylamino-propoxy)benzoyl]7-methylsulfonamido benzofuran oxalate (Ex. 121)
M.p.: 81° C. (isopropanol/diethyl ether)
Purity (HPLC): 96.1%

2-n-butyl 3-[4-(3-di-n-butylamino-propoxy)3,5-di-tert.butyl benzoyl]5-methylsulfonamido benzofuran oxalate (SR 34569 A) (Ex. 122)
M.p.: 151° C. (ethyl acetate/heptane)

2-phenyl 3-[4-(3-di-n-butylamino-propoxy)benzoyl]6-methylsulfonamido indolizine oxalate (SR 34203 A) (Ex. 123)
Amorphous yellow powder 2-phenyl 3-{4-[3-(N-methyl N-3,4-dimethoxy-β-phenethyl)amino-propoxy]benzoyl} 7-methylsulfonamido indolizine hydrochloride (SR 34552 A) (Ex. 124)
M.p.: 110° C. (methanol/water)

2-phenyl 3-[4-(3-di-n-butylamino-propoxy)benzoyl[7-carbethoxy indolizine oxalate (SR 34547 A) (Ex. 125)
Amorphous yellow powder 7-amino 3-[4-(3-di-n-butylamino-propoxy)benzoyl]2-n-butyl indolizine (SR 34399 A) (Ex. 126)
M.p.: 88°-89° C. (n-hexane)

3-[4-(3-di-n-butylamino-propoxy)benzoyl]2-n-butyl 7-tolylsulfonamido indolizine (SR 34428 A) (Ex. 127)
Amorphous yellow powder 7-amino 3-{4-[3-(N-methyl N-3,4-dimethoxy-β-phenethyl)amino-propoxy] benzoyl} 2-phenyl indolizine (SR 34548 A) (Ex. 128)
M.p.: 115°-117° C. (dichloromethane/methanol)

2-n-butyl 3-{4-[3-(N-methyl N-3,4-dimethoxy-β-phenethyl)amino-propoxy] benzoyl} 7-bismethylsulfonamido indolizine oxalate (SR 34509 A) (Ex. 129)
Amorphous powder 2-n-butyl 3-{4-[3-(N-methyl N-3,4-dimethoxy-β-phenethyl)amino-propoxy] benzoyl} 7-methylsulfonamido indolizine sesquioxalate (SR 34534 A) (Ex. 130)
Amorphous yellow powder 2-phenyl 3-[2-(3-di-n-butylamino-propoxy)benzoyl]7-carbethoxy indolizine hydrochloride (SR 34550 A) (Ex. 131)
M.p.: 216°-218° C. (ehtyl acetate/methanol)

2-phenyl 3-[3-(3-di-n-butylamino-propoxy)benzoyl]7-carbethoxy indolizine oxalate (SR 34507 A) (Ex. 132)
Amorphous yellow powder

EXAMPLE 133

A capsule containing the following ingredients was prepared according to known pharmaceutical procedures:

| Ingredient | mg |
|---|---|
| Compound of the invention | 100.0 |
| Starches | 99.5 |
| Colloidal silica | 0.5 |
| | 200.0 |

We claim:

1. A benzofuran, benzothiophene, indole or indolizine compound of formula:

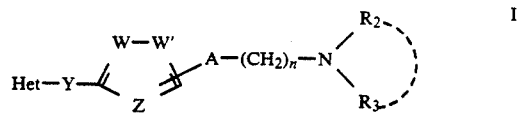

in which:

Het represents one of:

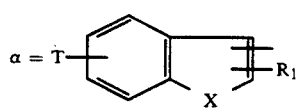

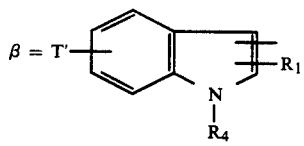

-continued

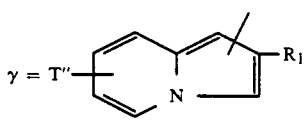

in which:

T represents:

in which:
R and $R_a$, identical or different, represent:
hydrogen,
$C_1$-$C_4$ alkyl
$SO_2R'$ in which R' represents a linear or branched $C_1$-$C_6$ alkyl, trifluoromethyl, phenyl, phenyl substituted by a $C_1$-$C_4$ alkyl, benzyl, benzyl substituted by $C_1$-$C_4$ alkyl, benzoyl or benzoyl substituted by $C_1$-$C_4$ alkyl, and $R_a$ and R' forming with the nitrogen atom to which they are attached a ring bearing from 3 to 6 carbon atoms, T' represents:
hydrogen
nitro

as previously defined,

T" represents:
benzyloxycarbonylamino

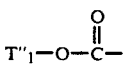

in which $T''_1$ represents hydrogen or $C_1$-$C_4$ alkyl

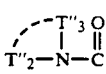

in which $T''_2$ and $T''_3$, identical or different, represent hydrogen or $C_1$-$C_4$ alkyl or $T''_2$ and $T''_3$ form with the nitrogen atom to which they are attached a ring having from 4 to 6 carbon atoms

as defined previously
X represents —O— or —S—
Y represents

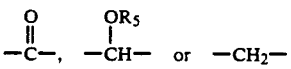

in which $R_5$ represents hydrogen, $C_1$-$C_4$ alkyl or an acyl of formula

in which $R'_4$ represents $C_1$-$C_4$ alkyl $R_1$ represents $C_1$-$C_6$ alkyl, phenyl, phenyl substituted by $C_1$-$C_4$ alkyl or halogenophenyl $R_2$ represents:
hydrogen
a linear or branched $C_1$-$C_6$ alkyl $R_3$ represents:
a linear or branched $C_1$-$C_6$ alkyl
Alk—$R_6$ in which Alk represents a simple bond or a linear or branched $C_1$-$C_5$ alkylene and $R_6$ represents pyridyl, phenyl, phenoxy, 3,4-methylenedioxy phenyl or phenyl or phenoxy substituted by one or more substituents, identical or different, selected from halogen, $C_1$-$C_4$ alkyl or $C_1$-$C_4$ alkoxy, $R_2$ and $R_3$, when they are taken together, represent $C_3$-$C_6$ alkylene or alkenylene or $C_3$-$C_6$ alkylene or alkenylene substituted by phenyl, 3-oxo-1,5-pentamethylene, 3-aza 1,5-pentamethylene, 3-methylaza 1,5-pentamethylene, 3-phenylaza 1,5-pentamethylene or —CH—CH—N=CH—, $R_4$ represents:
hydrogen
$C_1$-$C_4$ alkyl
—$SO_2$ $R'_1$ in which $R'_1$ represents $C_1$-$C_4$ alkyl, phenyl, phenyl substituted by $C_1$-$C_4$ alkyl, benzyl, or benzyl substituted by $C_1$-$C_4$ alkyl

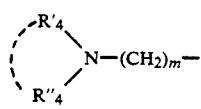

in which $R'_4$ and $R''_4$, identical or different, represent $C_1$-$C_4$ alkyl and m represents an integer from 1 to 3

A represents —O—, —S— or

W, W' and Z are such that:
when identical, W and W' represent

or N, Z represents —O— or —S—
when W represents

and W' represents

Z represents —CH=C'—R'$_8$

R$_8$ and R'$_8$ being identical or different and representing hydrogen, a halogen atom, C$_1$-C$_4$ alkyl or C$_1$-C$_4$ alkoxy, n represents an integer from 1 to 5 provided that when R$_4$ represents —SO$_2$R'$_1$, T' represents hydrogen, nitro or cyclised

or a pharmaceutically acceptable salt thereof.

2. A compound according to claim 1 in which R represents —SO$_2$R' and R$_a$ represents hydrogen.

3. A compound according to claim 1 in which Y represents

4. A compound according to claim 1 in which the moiety

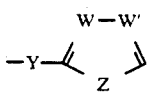

represents benzoyl.

5. A compound according to claim 1 in which the moiety

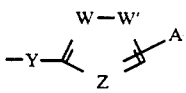

represents 4-benzoyl oxy.

6. A compound according to claim 1 in which R$_1$, R$_2$ and R$_3$ represent n-butyl and n represents 3.

7. A compound according to claim 1 in which X represents —O—.

8. A compound according to claim 1 in which the chain

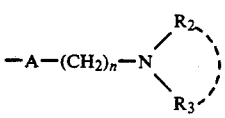

is at position 4.

9. A compound according to claim 1 in which the pharmaceutically acceptable salt is the oxalate, fumarate, hydrochloride or p-toluenesulfonate.

10. A compound according to claim 1 selected from:
2-n-butyl 3-[4-(3-di-n-butylamino-propoxy)benzoyl]5-methylsulfonamido benzofuran,
2-n-butyl 3-{4-[3-(N-methyl N-3,4-dimethoxy-β-phenethyl)aminopropoxy]benzoyl} 5-methylsulfonamido benzofuran,
2-isopropyl 3-[4-(3-di-n-butylamino-propoxy)benzoyl]5-methylsulfonamido benzofuran,
5-amino 3-[4-(3-di-n-butylamino-propoxy)benzoyl]2-n-butyl 1-methyl indole,
or pharmaceutically acceptable salts thereof.

11. A pharmaceutical composition containing as active ingredient at least one derivative of benzofuran, benzothiophene, indole or indolizine according to claim 1, in combination with a pharmaceutical vehicle or excipient.

12. A pharmaceutical composition containing as active ingredient at least one derivative according to claim 10, in combination with a pharmaceutical vehicle or excipient.

13. A method for the treatment of angina pectoris comprising administering to an animal in need thereof a pharmaceutical composition according to claim 11 containing from 50 to 500 mg of active ingredient.

14. A method of using at least one derivative of benzofuran, benzothiophene, indole or indolizine according to claim 1 comprising combining the derivative with a pharmaceutical vehicle or a suitable excipient for the production of a medicine designed for the treatment of angina pectoris.

15. A method for the treatment of hypertension comprising administering to an animal in need thereof a pharmaceutical composition according to claim 11 containing from 50 to 500 mg of active ingredient.

16. A method for the treatment of arrhythmias comprising administering to an animal in need thereof a pharmaceutical composition according to claim 11 containing from 50 to 500 mg of active ingredient.

17. A method for the treatment of cerebral circulatory insufficiency comprising administering to an animal in need thereof a pharmaceutical composition according to claim 11 containing from 50 to 500 mg of active ingredient.

18. A method of using at least one derivative of benzofuran, benzothiophene, indole or indolizine according to claim 1 comprising combining the derivative with a pharmaceutical vehicle or a suitable excipient for the production of a medicine designed for the treatment of hypertension.

19. A method of using at least one derivative of benzofuran, benzothiophene, indole or indolizine according to claim 1 comprising combining the derivative with a pharmaceutical vehicle or a suitable excipient for the production of a medicine designed for the treatment of arrhythmias.

20. A method of using at least one derivative of benzofuran, benzothiophene, indole or indolizine according to claim 1 comprising combining the derivative with a pharmaceutical vehicle or a suitable excipient for the production of a medicine designed for the treatment of cerebral circulatory insufficiency.

21. A veterinary composition containing as active ingredient at least one derivative of benzofuran, benzothiophene, indole or indolizine according to claim 1, in combination with a pharmaceutical vehicle or excipient.

22. A method for the treatment of angina pectoris comprising administering to an animal in need thereof a veterinary composition according to claim 11 containing from 50 to 500 mg of active ingredient.

23. A method for the treatment of hypertension comprising administering to an animal in need thereof a veterinary composition according to claim 11 containing from 50 to 500 mg of active ingredient.

24. A method for the treatment of arrhythmias comprising administering to an animal in need thereof a veterinary composition according to claim 11 containing from 50 to 500 mg of active ingredient.

25. A method for the treatment of cerebral circulatory insufficiency comprising administering to an animal in need thereof a veterinary composition according to claim 11 containing from 50 to 500 mg of active ingredient.

26. A veterinary composition containing as active ingredient at least one derivative according to claim 10, in combination with a pharmaceutical vehicle or excipient.

* * * * *

UNITED STATES PATENT AND TRADEMARK OFFICE
CERTIFICATE OF CORRECTION

PATENT NO. : 5,223,510
DATED : June 29, 1993
INVENTOR(S) : Jean Gubin et al.

It is certified that error appears in the above-indentified patent and that said Letters Patent is hereby corrected as shown below:

On the title page, Item [75], please add inventor -- Steven Kilenyi, Brussels, Belgium --.

Signed and Sealed this

Twenty-fourth Day of October, 1995

Attest:

BRUCE LEHMAN

*Attesting Officer*  *Commissioner of Patents and Trademarks*